United States Patent [19]
Rai

[11] Patent Number: 5,989,513
[45] Date of Patent: *Nov. 23, 1999

[54] BIOLOGICALLY ASSISTED PROCESS FOR TREATING SOUR GAS AT HIGH PH

[75] Inventor: Charanjit Rai, Kingsville, Tex.

[73] Assignee: Gas Research Institute, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/690,352

[22] Filed: Jul. 26, 1996

Related U.S. Application Data

[60] Provisional application No. 60/001,646, Jul. 28, 1995, and provisional application No. 60/001,647, Jul. 28, 1995.

[51] Int. Cl.$^6$ .............................. B01D 53/52; C01B 17/05
[52] U.S. Cl. ...................... 423/573.1; 423/220; 423/224; 423/576.6; 423/576.7; 423/576.8; 423/DIG. 17; 435/168; 435/266
[58] Field of Search .................................. 423/220, 224, 423/573.1, 576.6, 576.7, 576.8, DIG. 17; 435/168, 266, 282

[56] References Cited

U.S. PATENT DOCUMENTS

| | | | |
|---|---|---|---|
| 3,218,252 | 11/1965 | Glover et al. | 210/611 |
| 3,266,889 | 8/1966 | Duncan et al. | 435/262 |
| 3,305,353 | 2/1967 | Duncan et al. | 435/262 |
| 4,206,288 | 6/1980 | Detz et al. | 435/267 |
| 4,455,287 | 6/1984 | Primack et al. | 423/573 |
| 4,456,688 | 6/1984 | Dugan et al. | 435/267 |
| 4,559,313 | 12/1985 | Myerson et al. | 502/25 |
| 4,622,212 | 11/1986 | McManus et al. | 423/226 |
| 4,666,852 | 5/1987 | Cork | 435/262 |
| 4,758,417 | 7/1988 | Van Lookeren-Campagne | 423/DIG. 17 |
| 4,760,027 | 7/1988 | Sublette | 435/266 |
| 4,789,478 | 12/1988 | Revis et al. | 210/611 |
| 4,861,723 | 8/1989 | Madgavkar | 435/262 |
| 4,888,293 | 12/1989 | Hackl et al. | 435/245 |
| 4,891,205 | 1/1990 | Bedell | 423/576.6 |
| 4,931,262 | 6/1990 | Sonta et al. | 423/224 |
| 4,987,081 | 1/1991 | Hackl et al. | 435/262 |
| 5,021,069 | 6/1991 | Whellock et al. | 44/622 |
| 5,089,412 | 2/1992 | Hackl et al. | 435/252.4 |
| 5,096,691 | 3/1992 | Bedell | 423/576.6 |
| 5,338,778 | 8/1994 | Bedell | 423/220 |
| 5,508,014 | 4/1996 | Rai | 423/224 |
| 5,686,293 | 11/1997 | Jenneman et al. | 435/252.1 |
| 5,747,331 | 5/1998 | Hartikainen et al. | 435/266 |

FOREIGN PATENT DOCUMENTS

| | | | |
|---|---|---|---|
| 0 220 776 A2 | 10/1986 | European Pat. Off. | |
| 61-133123 | 6/1986 | Japan | 423/DIG. 17 |
| 63-205124 | 8/1988 | Japan | 423/224 |
| 1557164 | 4/1990 | U.S.S.R. | 435/168 |

OTHER PUBLICATIONS

"Microorganisms in Reclamation of Metals" by Hutchins et al., Ann. Rev. Microbiol., 1986 No Month, vol. 40, pp. 311–335.

"Microbial Sweetening of Sour Gas," P.N. Agumadu and Charanjit Rai, 1991 GRI Liquid Redox Sulfur Recovery Conference, Austin, Texas, May 5–7, 1991, GRI 91/0188.

(List continued on next page.)

*Primary Examiner*—Gary P. Straub
*Assistant Examiner*—Timothy C Vanoy
*Attorney, Agent, or Firm*—Pauley Petersen Kinne & Fejer

[57] ABSTRACT

A process for biologically enhancing an iron-based redox process for catalytic oxidation of a sulfide compound such as hydrogen sulfide from a gas in a redox system wherein said catalyst comprises a ferric compound and at least one organic chelant capable of holding ferric and ferrous ions in solution at processing temperatures and conditions suitable for generation and retrieval of elemental sulfur, comprising the steps of oxidation of a sulfide compound by a gas with a redox system comprising ferric ions, removal of elemental sulfur from said system, and reoxidation of ferrous ions in the redox system in the presence of a culture of bacteria comprising *Thiobacillus ferrooxidans* and leptospirillium ferrooxidans at a pH at least as high as about 7.5.

9 Claims, 29 Drawing Sheets

OTHER PUBLICATIONS

"Growth and Maintenance of *Thiobacillus ferrooxidans* Cells," Jean LaCombe Barron and Donald R. Lueking, pp. 2801, 2804, *Applied and Environmental Microbiology*, vol. 56 No. 9, Sep. 1990.

S.I.R. H1074, Lazaroff et al., Bacterio–Electric Leaching of Metals, Jul. 7, 1992.

"Studies on Bacteria In The ANG Stretford Plant," by Mary C. Bromel, Ph.D., *Proceedings of the 1986 Stretford Users' Conference*, Austin, Texas, May 5–6, 1986, pp. 176, 186, GRI 86/0256.

"Ferrous Iron Oxidation By *Thiobacillus ferrooxidans*," by W. John Ingledew, *Biotechnology and Bioengineering Symp. No. 16*, Workshop on Biotechnology for the Mining, Metal–Refining and Fossil Fuel Processing Industries, p. 24, 1986 No Month.

"Microbial Mining Boosts the Environment, Bottom Line," pp. 778, 779, *Science*, vol. 264, pp. 745–846, May 6, 1994 by Anne Simon Moffat.

"Early Experience With LO–CAT 11™ For Natural Gas Treatment," L.C. Hardison (ARI Technologies, Inc.), presented at AIChE Spring Meeting, Mar. 29–Apr. 2, 1992.

"Biologically–Enhanced Redox Solution Reoxidation" by C. Rai and J. Rao, Proceedings of the GRI 1994 Sulfur Recovery Conference, pp. 199–214, May 15–17, 1994.

"Bacteria Help Desulfurize Gas," H. Satoh, J. Yoshizawa and S. Kametanl, *Hydrocarbon Processing*, May 1988, pp. 76–D to 76–F.

"Microbial Sweetening of Sour Natural Gas Using Mixed Cultures," by Charanjit Rai and Martin Taylor, *Environmental Progress*, Spring, 1996. vol. 15 No. 1.

"Microbial Enhancement For Liquid Redox Systems—Data For A U.S. Patent Application, 'An Improved Liquid Redox System Using Microbes,'" by Texas A&I University, Department of Chemical & Natural Gas Engineering, submitted to Gas Research Institute on Sep. 28, 1992.

"Processing and Utilization of High Sulfur Coals," edited by Yosry A. Attia, *Coal Science and Technology 9*, Proceedings of The First International Conference on Processing and Utilization of High Sulfur Coals, Oct. 13–17, 1985.

"Modelling of $Fe^{2+}$ oxidation by *Thiobacillus ferrooxidans*," by Shrihari, R. Kumar, and K.S. Gandhi, *Applied Microbiology and Biotechnology*, (1990) 33:524–528.

"Microbial Sweetening of Sour Gas Using Acidophilic Chilean Cultures," by Ajay K. Singh and C. Rai, Texas A & M University, Paper No.: 18th, prepared for presentation at the 1995 Summer National Meeting of AIChE; Biotreating of Gas Streams, Jun., 1995.

"Recent Developments In Acid Gas Treatment Using The Autocirculation Lo–Cat(R) Approach," by L.C. Hardison, ARI Technologies, Inc., for presentation at the AIChE 1990 Spring National Meeting, Apr. 7–11, 1991.

"Case History—Lo–Cat® $H_2S$ Oxidation System For Town Of Jupiter, Florida," by Robert F. Eaton, ARI Technologies, Inc., for presentation at GRI Liquid Redox Sulfur Recovery Conference, Oct. 4–6, 1992.

"Solutions to $H_2S$ removal—The Town of Jupiter, Florida, Uses Lo–Cat® Unit to Solve Odor Problem in Water Treatment Plant," brochure by Wheelabrator Clean Air Systems Inc. Dec. 1992.

"Solutions to $H_2S$ removal—Lo–Cat II® Unit Exceeds $H_2S$ Removal Efficiency Requirements in Treatment of Wellhead Casing Gas," brochure by Wheelabrator Clean Air, Wheelabrator Technologies Inc. Dec. 1992.

"An Overview of Liquid Redox Sulfur Recovery," by D.A. Dalrymple, T.W. Trofe, and J.M. Evans, *Chemical Engineering Progress*, pp. 43–49, Mar., 1989.

"Technical and Economic Comparison of LO–CAT II™ with other Iron–Based Liquid Redox Processes," by M. P. Quinlan and L. W. Echterhoff, Paper presented at the 1992 GRI Liquid Redox Sulfur Recovery Conference in Austin, Texas, Oct. 4–6, 1992.

"Gas Research Institute Program in Sulfur Removal and Recovery Research—1992 Update," by D. Leppin, Proceedings of the 1992 Liquid Redox Sulfur Recovery Conference in Austin, Texas, Oct., 1992.

"LO–CAT II™—A Big Step Forward in Iron Redox Chemistry," by Hardison Proceedings of the 1991 Liquid Redox Sulfur Recovery Conference in Austin, Texas, pp. 181–200, May, 1991.

"Kinetics of Liquid Phase Oxidation of Acid Ferrous Sulfate by the Bacterium *Thiobacillus ferrooxidans*," by D.T. Lacey and F. Lawson, *Biotechnology and Bioengineering*, vol. XII, Issue 1, pp. 30–50, 1987.

"Molecular Genetics of *Thiobacillus ferrooxidans*," by D.E. Rawlings and T. Kusano, *Microbiological Reviews*, vol. 58, No. 1, pp. 39–55, Mar., 1994.

"Process Optimization for Microbial Sweetening of Sour Natural Gas," by R.R. Gokarn , M.S. Thesis (Abstract), Texas A&I University, Aug. 1993.

"Iron Oxidation and Energy Conservation in Chemoautotroph *Thiobacillus ferrooxidans*," by John C. Cox and Martin D. Brand, Edited by W.R. Stroht and O.H. Touvinen, *Microbial Chemoautotrophy*, pp. 31–46, 1984.

"A Novel Microbial Sweetening Process for Sour Natural Gas Upgrading," by H.K. Dinesh–Mohan, M.S. Thesis (Abstract), Texas A&I University, 1992.

"Microbial Desulfurization of Coals in a Slurry Pipeline Reactor Using *Thiobacillus ferrooxidans*" by Charanjit Rai, *Biotechnology Progress*, vol. 1, No. 3, pp. 200–204, Sep. 1985.

"GRI Program in Sulfur Removal and Recovery from Natural Gas—1994 Update," by D. Leppin, Paper presented at GRI Sixth Sulfur Recovery Conference in Lakeway, Texas, May 15–17, 1994.

"Chelates' Role in Gas Treating," by S.A. Bedell, L.H. Kirby, C.W. Buenger and M.C. McGaugh, *Hydrocarbon Processing*, pp. 63–66, Jan., 1988.

"Application of Iron–Oxidizing Bacteria to Hydrometallurgical Flue Dust Treatment and $H_2S$ Desulferization," by T. Shiratori and H. Sonta, *FEMS Microbiology Reviews*, 11, 1993, pp. 165–174.

"Microbial Mining Boosts the Environment, Bottom Line," by A. S. Moffat, *Science*, vol. 264, pp. 778–779, May 6, 1994.

"Mineral Biotechnology," by A. Bruynesteyn, *Journal of Biotechnology*, 11:1–10, 1989; Elsevier.

"Acidic Mine Drainage: the Rate Determining Step," by P.C. Singer and W. Stumm, *Science*, vol. 167, pp. 1121–1123, Feb. 1970.

"Desulfuring of Natural Gas and Petroleum Oil by Autotrophic *Thiobacillus ferrooxidans*," by Amitabha Das, Pradosh Roy, and Ajit K. Mishra, *Letters in Applied Microbiology*, 1993, vol. 16, 164–166.

"The Microbiology of Mine Drainage Pollution," by D.G. Lundgren, J.R. Vestal, and F.R. Tabita, In R. Mitchell (ed.), *Water Pollution Microbiology*, pp. 69–88, 1972.

"A Proposed Mechanism for Energy Conservation During $Fe^{2+}$ Oxidation by *Thiobacillus ferrooxidans:* Chemiosmotic Coupling to Net H+ Influx," by W.J. Ingledew, J.C. Cox, and P.J. Halling, *FEMS Microbiology*, Letters 2, pp. 193–197, 1977.

"The Purification and Some Properties of Rusticyanin, a Blue Copper Protein Involved in Iron(II) Oxidation from *Thiobacillus ferrooxidans,*" by J.C. Cox and D. H. Boxer, *Biochem. J.* 174: 497–502, 1978.

"Role of a Ferric Ion–Reducing System in Sulfur Oxidation of *Thiobacillus ferrooxidans,*" by T. Sugio, C. Domatsu, O. Munakata, T. Tano, and K. Imai, *Applied and Environmental Microbiology*, vol. 49, No. 6, pp. 1401–1406, Jun. 1985.

"Energy Supply for the Chemoautotroph *Ferrobacillus ferrooxidans,*" by P.R. Dugan and D.G. Lundgren, *Journal of Bacteriology*, vol. 89, No. 3, pp. 825–834, Mar. 1965.

"Carbon Dioxide Fixation in the Chemoautotroph, *Ferrobacillus ferrooxidans,*" by W.J. Maciag and D.G. Lundgren, *Biochemical and Biophysical Research Communications*, vol. 17, No. 6, pp. 603–607, 1964.

"Adenosine Triphosphate–Dependant Reduction Nicotinamide Adenine Dinucleotide by Ferro–Cytochrome C In Chemoautotrophic Bacteria," by M.I.H. Aleem, H. Lees, and D.J.D. Nicholas, *Nature*, vol. 200, pp. 759–761, Nov. 23, 1963.

"The Direct Linear Plot: A New Graphical Procedure for Estimating Enzyme Kinetic Parameters," by Robert Eisenthal and Athel Cornish–Bowden, *Biochem. J.*, vol. 139, pp. 715–720, 1974.

*Handbook of Microbiological Media,* by Ronald M. Atlas, pp. 892–893, CRC Press, 1993.

"Growth of *Ferrobacillus ferrooxidans* on Organic Matter," by F. Shafia and Richard F. Wilkinson, Jr., *J. Bacteriol.*, vol. 97, pp. 256–260, 1969 (Jan.).

"Scanning Electron Microscopic Examination of *Thiobacillus ferrooxidans* on Different Support Matrix Materials in Packed Bed and Fluidized Bed Bioreactors," by S.I. Grishin, and O.H. Tuovinen, *Applied Microbiology and Biotechnology*, vol. 31, 505–511, 1989.

"Bacteria Help Desulfurize Gas," by H. Satoh, J. Yoshizawa, and S. Kametani, *Hydrocarbon Processing*, pp. 76D–76–F, May 1988.

"Catalytic Conversion of Gas Impurities," by Arthur L. Kohl and Fred C. Reisenfeld, *Gas Purification, Third Edition*, pp. 657–661, 675–678, 1979.

"Chemical Composition of Discovered and Undiscovered Natural Gas in the United States—1993 Update, vol. 1: Project Summary," by R.H. Hugman, P.S. Springer, and E.H. Vidas Dec. 1993; GRI–93/0456.1.

"Gas Research Institute Program in Natural Gas Processing," by D. Leppin and H.S. Meyer, Paper SPE 21505 presented at SPE Gas Technology Symposium, Jan. 23–25, 1991.

1. AGITATOR
2. REDOX PROBE
3. SAMPLE DRAW
4. H2S/AIR INLET
5. AGITATOR SUPPORT
6. HEATING ELEMENT
7. TEMP. SENSOR
8. AGITATOR SUPPORT
9. H2S OUTLET

BIOLOGICALLY ASSISTED PROCESS FOR TREATING SOUR GAS AT HIGH PH

This application claims the benefit of U.S. Provisional Application 60/001,646 filed Jul. 28, 1995, and U.S. Provisional Application 60/001,647 filed Jul. 28, 1995.

BACKGROUND OF THE INVENTION

This invention relates to the use of acidophilic bacteria, such as *Thiobacillus ferrooxidans* to regenerate chelated polyvalent catalysts (chelating agents) used in the oxidation of hydrogen sulfide to elemental sulfur for enhanced economics in sweetening of sour natural gas. More particularly, the invention relates to biologically enhancing the production of elemental sulfur and enhancing the thermal stability of the costly chelating agents during the operation of a hydrogen sulfide removal process in which said catalysts are regenerated.

Treatment of Sour Natural Gas

The natural gas industry has long been interested in sulfur recovery technology for applications to gaseous streams resulting from the treatment of sour natural gas resources to render them commercially useful. Many natural gas resources contain significant quantities of hydrogen sulfide ($H_2S$) and other contaminants. Such "sour" gas is hazardous to human health and could cause extensive damage to natural gas pipelines if not properly processed. In order to reduce health and environmental hazards, and to meet the pipeline industry specifications, the $H_2S$ concentrations in natural gas are ordinarily reduced to less than 4 parts per million in volume (ppmv). About twenty five percent of the natural gas produced in the United States contains significant volumes of $H_2S$ and other sulfur compounds.

A traditional process for treating this sour gas is the Amine-Claus process which involves a two-step approach of first separating the acidic gases from the natural gas in an Amine plant and then either flaring the hydrogen sulfide off or recovering the sulfur in a separate Claus plant. Liquid redox processes, such as the Stretford process, are commonly preferred over the Amine-Claus systems because of their greater simplicity, higher sulfur recovery and good turndown ratio. Exemplary references more particularly describing these matters include U.S. Pat. Nos. 4,009,251; 4,243,648; and 3,937,795. Scavenger processes are preferred for natural gas streams where sulfur recovery is not economical.

Liquid redox sulfur recovery processes absorb hydrogen sulfide from the sour gas stream, ultimately producing elemental sulfur. Liquid redox processes may use, for example, vanadium, iron or a mixture of iron and quinone as the primary catalysts interacting with hydrogen sulfide.

The Stretford liquid redox process uses vanadium as the catalyst. Unfortunately, vanadium is toxic at any concentration and environmental regulations prevent its disposal at concentrations above 25 ppm. On the other hand, iron based catalyst systems are generally preferable because of their non-toxic, generally environmentally friendly character. The iron-based catalyst systems have been successful because of their superior performance, simple operation, greater reliability, as well as their environmental acceptability. A recognized drawback to the iron-based systems is that the commercial processing conditions promote oxidation reactions and thereby accelerate the decomposition of the metal-chelate catalysts essential for the reaction, resulting in undesirably high processing costs, including increasing recirculation power requirements. Moreover, in all the commercial liquid redox processes, expensive redox solution is inevitably lost via salt formation and unrecoverable residue in the sulfur cake resulting from the process.

In the late 1970's, ARI Technologies of Palatine, Ill., developed a liquid redox process under the trade name LO-CAT®, which has undergone a number of refinements aimed at improved reliability and economics. In 1987, Shell/DOW introduced a liquid redox process under the trade name SulFerox®, which uses a scrubbing solution containing 2 to 4 weight percent of iron. This process provides relatively high $H_2S$ removal capacity for a given volume of solution.

Iron based redox processes employ iron in the ferric state ($Fe^{3+}$) to oxidize hydrogen sulfide in a stream of sour gas to elemental sulfur ($S^0$), whereby the ferric iron is reduced to the ferrous state ($Fe^{2+}$), which is then regenerated to the ferric state by oxidation with air as follows:

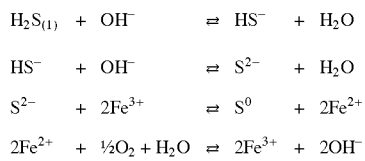

Typical iron concentrations range from 500–2500 ppm in the catalyst. Concentrations are varied according to economics of pumping and chemical costs attributable to the specialized circumstances of particular applications and processing facilities.

Neither ferric nor ferrous ions are stable in aqueous solutions at neutral or alkaline pH levels and will, therefore, ordinarily precipitate as either ferric or ferrous hydroxide. This precipitation is inhibited by complexing the iron with organic chelates which are capable of holding both $Fe^{2+}$ and $Fe^{3+}$ ions in solution over the wide range of pH typically encountered during commercial processing.

The organic chelates utilized in these redox systems are ordinarily classified into two groups: type A chelates such as ethylenediamine tetraacetic acid (EDTA) or nitrilotriacetic acid (NTA), powerful chelating agents at low pH; and the type B chelates, consisting of polyhydroxylated sugars (saccharides) that are effective at pH above 8. A proprietary combination of both types of chelates results in a catalyst that is stable over a range of pH, for example, from 5 to 9.0.

In work with the LO CAT process, McManus disclosed, in U.S. Pat. No. 4,622,212 (incorporated herein by reference), the desirability of combining an aminopolycarboxylic acid chelating agent (type A) with a polyhydroxylated saccharide (type B) chelating agent. McManus observed that chemical degradation and loss of the aminopolycarboxylic acid chelating agent, thereby necessitating addition of replacement chelating agent is the single most significant operating problem affecting the ultimate economic feasibility of prolonged large-scale operation of this liquid redox process. McManus and others have suggested the use of additional stabilizing agents or additives to the catalyst system, such as alkaline thiosulfate, t-butanol and ethylene glycol. According to the literature, even in the presence of such stabilizing agents, only limited stability of the commercial chelating agents at processing temperatures in excess of 35° C. has been attained.

The aminopolycarboxylic acid chelants such as nitrilotriacetic acid (NTA), ethylenediaminetetraacetic acid (EDTA), N-hydroxyethylenediamine tetraacetic acid (HEEDTA), and diethylenetriamine pentaacetic acid (DTPA) are powerful chelating agents at low pH. The polyhydroxylated saccharide chelants, such as sorbitol, are effective at pH above 8.0.

The combination of multiple chelants selected from both groups can result in a catalyst system that is stable over a wide range of pH, from 2 to 10.0.

Liquid Redox Process Degeneration Products in Iron Based Redox Processes

The selection of particular chelants is dependent on the reaction rate of (1) the $Fe^{3+}$ chelate with $H_2S$, (2) the reaction rate of the $Fe^{2+}/Fe^{3+}$ chelate with oxygen, and (3) the rate of degradation of the chelate. Ferric ion oxidation of the chelate can be controlled by maintaining the overall reaction temperature below 45° C. Chelate degradation occurs through the oxidation of chelate by $Fe^{3+}$ ion and free radical induced oxidation. Other variables that control the oxidative degradation are pH, chelate concentration, chelate to iron ratio, and the type of degradation products formed under process conditions.

The LO-CAT® process was originally developed by ARI Technologies, now Wheelabrator Clean Air Systems, Inc. (WCAS), to treat sour gas in an absorber vessel where the absorption of the $H_2S$ and oxidation to sulfur takes place and a reoxidation where the chelated iron is reactivated by oxidation by exposure to air in a stirred reaction chamber. This system, referred to as "conventional" LO-CAT, works well for many low-pressure plants at feed gas pressure and relatively low iron concentrations (1000 to 1500 ppmw) and high circulation rates. This system requires prohibitively expensive equipment and pumping costs for high pressure applications, however.

Modifications to the original LO-CAT® process, referred to as the ARI LO-CAT II process (shown in the FIG. 1 process flow diagram) were developed for high pressure "direct treat" applications. The LO-CAT II® process uses substoichiometric iron chelated catalysts in the absorber and an oxidizer unit that circulates liquid through density differences. This "staged" oxidation of the LO-CAT II system circulates throughout the solution by means of density differences generated by controlled aeration, such as by sparging, with oxidizing air, rather than by a mechanically well-stirred reaction chamber (WSTR). Solutions are withdrawn from the oxidizer at the last, or most oxidized stage. This delayed withdrawal or "draw down" involves the overall oxygen mass transfer and thereby permits the design of smaller oxidizers. Ratios of iron to $H_2S$ as low as 20% of the stoichiomatic requirement have been reported as successfully utilized. The process also uses a separate sulfur settler vessel. These features reduce both the chemical and operating costs.

Mechanism of Microbial Oxidation of Ferrous Iron

Thiobacillus ferrooxidans, an iron oxidizing bacterium discovered in 1947, has been used since 1984 in Japan to regenerate an iron based sour gas treating solution without catalysts, and without side reactions such as formation of thiosulfuric acid, at an acidic pH of about 2, as described by H. Satoh, et al., of the NKK Corporation in Hydrocarbon Processing, May, 1988, incorporated herein by reference.

The iron oxidizing bacteria are, by definition, capable of oxidizing ferrous ($Fe^{2+}$) ions to the ferric ($Fe^{3+}$) ion state at low pH. According to the literature, such bacteria are capable of oxidizing $Fe^{2+}$ to the $Fe^{3+}$ state at a rate about 500,000 times faster than in a non-biologically mediated chemical oxidation process in the absence of bacteria. In theory, these bacteria derive the energy required for their growth from the oxidation of reduced sulfur compounds and the oxidation of $Fe^{2+}$ to $Fe^{3+}$, using air as an oxidant.

The acidophilic iron bacteria, Thiobacillus ferrooxidans, generates ATP by a membrane bound ATP catalase. This ATP generating metabolism is driven by the proton motive force derived by the difference between the bacterium's neutral cytoplasm and its highly acidic environment to generate a transmeinbrane proton electrochemical potential. Neutralization of the bacterium's cytoplasm is catalyzed by the cytochrome oxidase reaction. The regeneration of $Fe^{3+}$ chelate in the presence of acidophilic microbes such as Thiobacillus ferrooxidans under mild conditions at 25–45° C., and atmospheric pressure minimizes the chelate degradation process and thus improves the economics of hydrogen sulfide oxidation in the commercial natural gas sweetening process. Another useful feature is that the regenerated $Fe^{3+}$-chelates are also capable of oxidizing the mercaptans to insoluble disulfides.

There is evidence that Thiobacillus ferrooxidans may not be one distinct bacterium, but rather a group of metabolically similar microbes. It has long been recognized that sulfur sequestration or removal is carried out by a variety of bacteria. Acidophilic bacteria that grow as heterotrophs include Acidiphilum cryptum and Thiobacillus acidophilus, while those that grow as autotrophs include Thiobacillus ferrooxidans, Thiobacillus thiooxidans and Leptospirillum ferrooxidans. Non-acidophilic bacteria that grow in sulfur containing media, usually in the presence of glucose as an energy source include species of Pseudomonas, Escherichia coli, and Thiobacillus novellus. The recognized optimum pH for growth of T. ferrooxidans on ferrous ion is about 2.0. The oxidation of ferrous (Fe II) to ferric (Fe III) thus occurs outside the cell wall, where such low pH would not be fatal to the cell, whereas reduction of oxygen occurs inside the cell membrane at a biologically acceptable pH of about 6.5. Cytochrome oxidase mediates transfer of electrons from outside the cell membrane. (W. J. Ingledew, "Ferrous Ion Oxidation by Thiobacillus ferrooxidans" Biotechnology and Bioengineering Symposium No. 16, pp. 23–32, (1986).)

According to Ingledew, the iron-oxidase system of Thiobacillus ferrooxidans is a membrane bound enzyme complex that spans the cytoplasmic membrane of the organism. The $Fe^{2+}$ oxidizing portion of the respiratory chain is short, consisting of four redox proteins: a blue colored rusticyanin (copper protein) and three cytochromes, a cytochrome oxidase, cytochrome c, and cytochrome a. (D. E. Rawlings and T. Kusano, "Molecular Genetics of Thiobacillus ferrooxidans" Microbiological Reviews 58 (1), pp. 39–55 (March, 1994).) The electron transfer components are organized in the cytoplasmic membrane in such a fashion as to couple $Fe^{2+}$ oxidation to the generation of a transmembrane proton electrochemical potential (or proton-motive force) ($\Delta P$), measured to be 250 mV. A diagrammatic representation of this electron transfer mechanism is shown in FIG. 2, in which "out" and "in" refer to the bulk phase and the cytoplasm, respectively. In the iron-oxidase complex, the copper (Cu) protein rusticyanin is thought to be the initial electron acceptor from $Fe^{2+}$. The midpoint potential ($E_m$) of rusticyanin has been measured to be 680 mV at pH 3.2. During the growth of Thiobacillus ferrooxidans, the electrical potential ($E_h$) of the $Fe^{2+}/Fe^{3+}$ couple has been found to increase from approximately 555 mV to 800 mV as the $Fe^{2+}$ is oxidized by the bacterial cells. The reduction of molecular oxygen is catalyzed by a cytochrome oxidase at a pH of 6.5 on the inside of the cytoplasmic membrane.

Enhancement of the catalytic systems utilized in processing sulfur compounds by Thiobacillus ferrooxidans is the subject of the inventor's prior patent, U.S. Pat. No. 5,508, 014 issued Apr. 16, 1996 and incorporated herein by reference. The culture of Thiobacillus ferrooxidans utilized in that patent is deposited as ATCC #55720 (Budapest Treaty Deposit, American Type Culture Collection, 12301 Parklawn Drive, Rockville, Md.).

SUMMARY OF THE INVENTION

This invention relates to the biological enhancement of the removal of hydrogen sulfide from a hydrogen sulfide containing liquid or gas by using a biologically moderated liquid catalyst redox system to oxidize the hydrogen sulfide into elemental sulfur. Typically, hydrogen sulfide gas can be removed from a gas stream by using a liquid catalyst containing ferric ions. During oxidation of the hydrogen sulfide, the ferric ions in the liquid catalyst are converted to ferrous ions and the hydrogen sulfide is oxidized to elemental sulfur. Eventually, the vast majority of ferric ions in the liquid catalyst are converted to ferrous ions and the oxidation of hydrogen sulfide stops. In present systems, the liquid catalyst is regenerated by sparging air through the spend liquid catalyst thereby oxygenating the liquid catalyst.

In the process of the invention, cultures containing *Thiobacillus ferrooxidans* bacterial cells cultured in high pH medium before inoculation are introduced to the spent liquid catalyst improving both the rate of regeneration of ferric ions and the thermal stability of the catalysts. Typically, the enhanced process can remove not only hydrogen sulfide from natural gas but other sulfur compounds such as carbonyl sulfide, methyl mercaptan, ethyl lnercaptan, other alkyl mercaptans and alkyl disulfides impurities. The generation of sodium thiosulfate or potassium thiosulfate as a metabolic by-product also acts to prevent degradation of the liquid catalyst. The liquid catalysts used with this process include members of the group comprising non-chelated ferric sulfate, ferric ethylenediamine tetraacetic acid, ferric nitrilotriacetate, and commercially chelated catalyst ARI 310 or ARI 340.

A characteristic of these catalysts is the presence of one or more polyhydroxy compounds as chelants, such as, for example, sorbitol. Biological degradation of sorbitol may indicate bacterial metabolization of an important chelant. This invention further relates to conducting the bacterial moderated catalysts at increased temperatures, which tends to reduce or eliminate sorbitol degradation, resulting in thermal stability of the catalyst. This invention additionally relates to the use of mixed cultures of selected bacteria to enhance the performance of the redox system at various temperatures and pH's, apparently by supplying nutrients to the different organisms without disturbing the catalytic chemistry or degrading the essential chelants.

BRIEF DESCRIPTION OF THE DRAWINGS

The nature and characteristic features of the invention will be more readily understood from the following description taken in connection with the accompanying graphs, in which.

DETAILED DESCRIPTION

Figure 1:
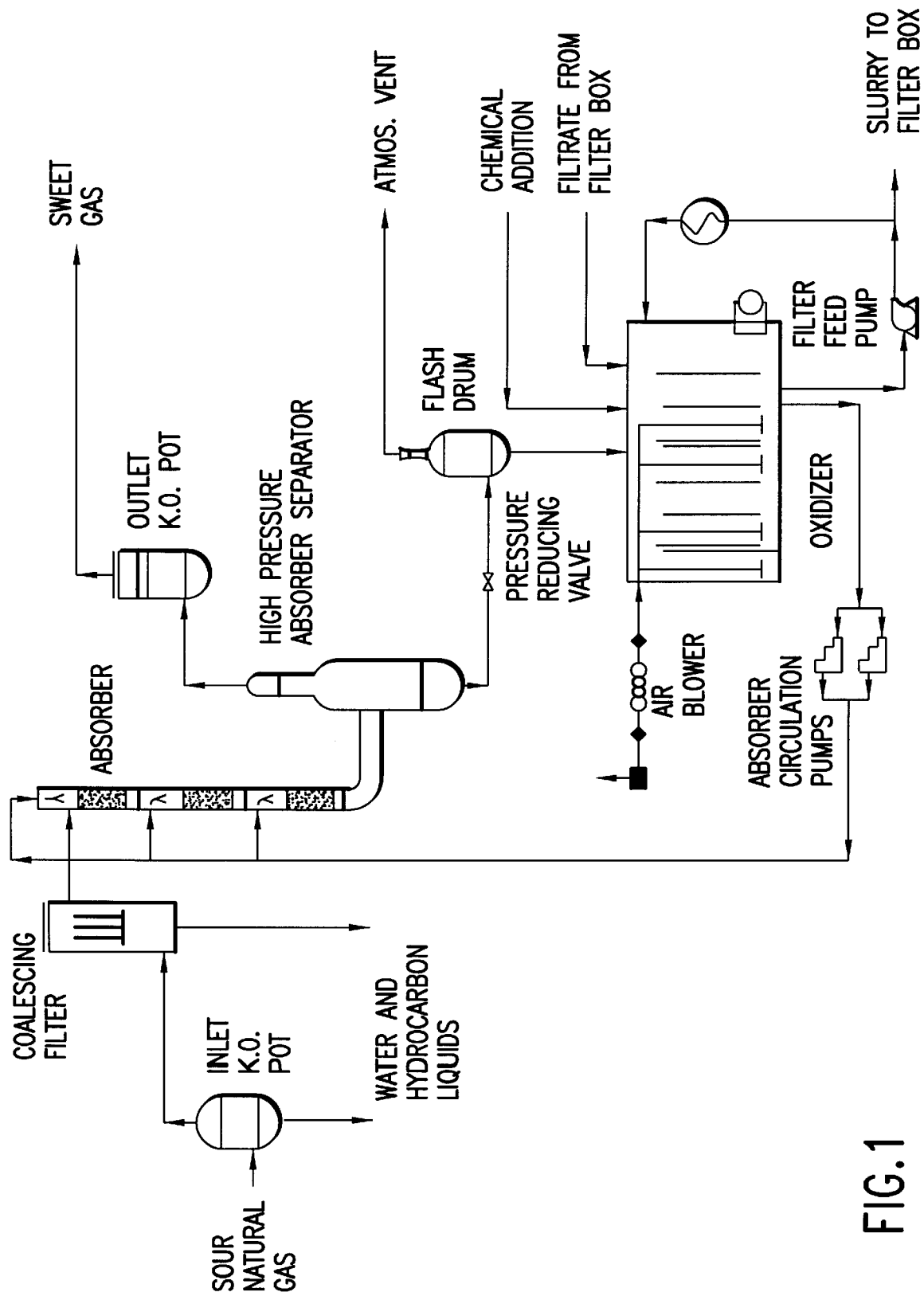
FIG. 1 is a process flow diagram for a liquid redox system.
Figure 2:
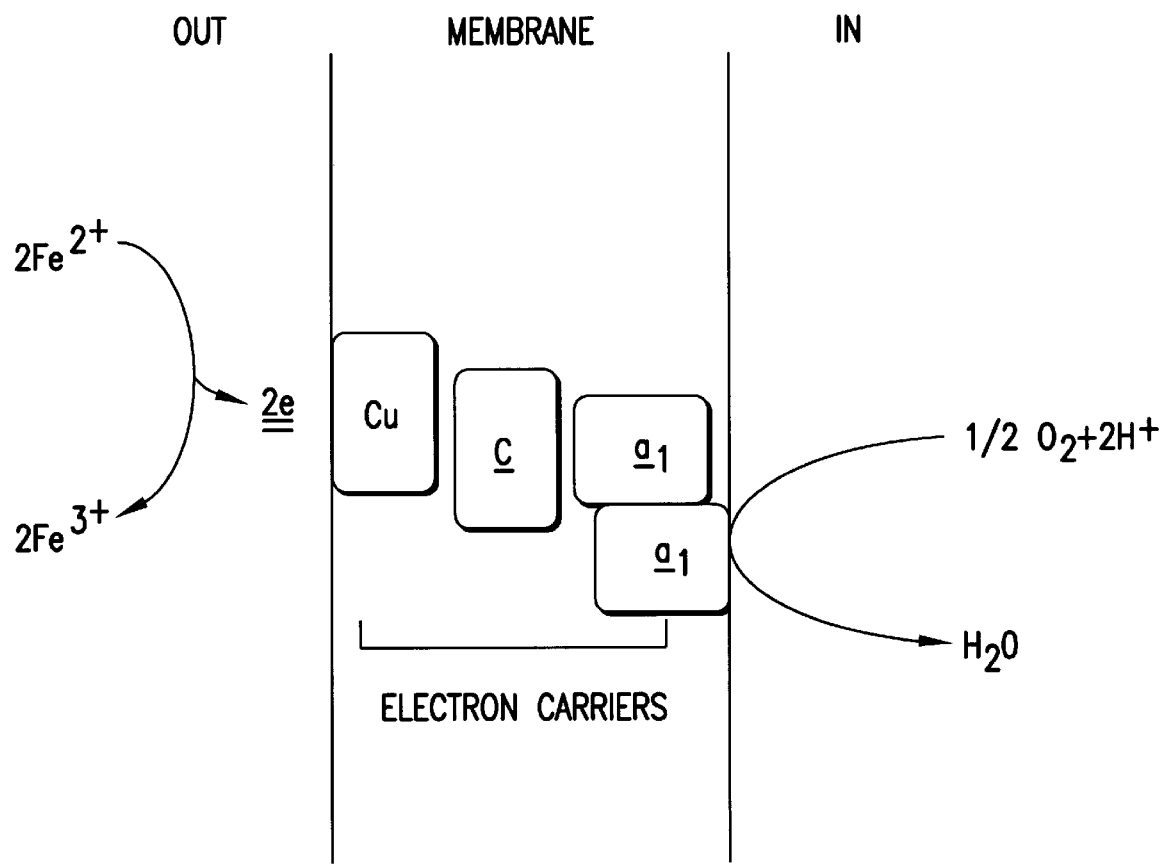
FIG. 2 is a diagram of a cell wall section according to Cobley, Haddock & Ingledew.

A pure culture of *Thiobacillus ferrooxidans* was obtained from the American Type Culture Collection (ATCC) (Reg. No. ATCC #23270). The cultures were subsequently maintained by serial transfers on a weekly basis, with separate cultures being maintained on two different media.

A first, ferrous sulfate based (ATCC #64), low pH culture media was prepared according to the following composition Solution A

| | |
|---|---|
| $(NH_4)_2SO_4$ | 0.4 g/L |
| $KH_2PO_4$ | 0.2 g/L |
| $MgSO_4.7H_2O$ | 0.08 g/L |
| De-Ionized $H_2O$ | 400 mL |

Solution B

| | |
|---|---|
| $FeSO_4.7H_2O$ | 10 g/L |
| $H_2SO_4$(1N) | 1 mL |
| De-Ionized $H_2O$ | 100 mL |

Solution A was autoclaved at 270° F., 20 psig for 15 minutes, cooled to room temperature and mixed with solution B.

A second, high pH culture media was prepared according to the following composition.

Composition Per Liter

| | |
|---|---|
| $Na_2S_2O_3.5H_2O$ | 10.0 g |
| $Na_2HPO_4.7H_2O$ | 7.9 g |
| Sodium Formate | 6.8 g |
| Glucose | 3.6 g |
| $KH_2PO_4$ | 1.5 g |
| $NH_4Cl$ | 0.3 g |
| $MgSO_4.7H_2O$ | 0.1 g |
| Trace metals sol. | 5.0 mL |

Trace Metals Solution
Composition Per Liter

| | |
|---|---|
| Disodium EDTA | 50.0 g |
| NaOH | 11.0 g |
| $CaCl_2.2H_2O$ | 7.34 g |
| $FeSO_4.7H_2O$ | 5.0 g |
| $MnCL_2.2H_2O$ | 2.5 g |
| $ZnSO_4.7H_2O$ | 2.2 g |
| $CoCl_2.6H_2O$ | 0.5 g |
| $(NH_4)_6Mo_7O_{24}.4H_2O$ | 0.5 g |
| $CuSO_4.5H_2O$ | 0.2 g |

Typically, 100 ml of media was placed in 500 mL Erlenmeyer flasks. These flasks were inoculated with 1 mL of ATCC 23270 *Thiobacillus ferrooxidans* cultured on ATCC #64K. The flasks were kept on a New-Brunswick Biological Shaker (Model G-33), maintained at 30° C. and 240 rpm. Pure cultures of *Thiobacillus ferrooxidans* were inoculated into the media. These microbes have been reported to lose their ability to oxidize or grow on ferrous ion after a number of transfers on ferrous ion-free glucose media. Accordingly, they were maintained by transfers into new media on a weekly basis and by fresh inoculations on a monthly basis.

The growth rate of *Thiobacilits ferrooxidans* was established by counting cells from the cultures with a Petroff-Hausser counting chamber under a phase contrast microscope at 20× and 40× magnifications at definite time intervals. Total number of cells per milliliter of the culture were calculated by using a factor of $2 \times 10^7$ to the observed cell count. A logarithmic growth rate was established. The maximum cell growth typically occurred in 25 to 35 hours resulting in a cell density of $1.5 \times 10^{11}$ cells/L in the high pH media.

The oxidation of hydrogen sulfide present in a synthetic sour gas stream representing sour natural gas was studied in a two-liter Virtis Omni-Culture Bioreactor. The synthetic sour gas had the following composition: hydrogen sulfide (0.71%), carbon dioxide (5.00%), and nitrogen (94.29%). Typically, a gas stream containing hydrogen sulfide can be oxidized into elemental sulfur when a liquid catalyst containing ferric ions is used. One of the problems in such a system is that ferric and ferrous ions have limited solubility in aqueous solution and tend to precipitate out of solution as ferric and ferrous hydroxide. This precipitation is prevented by complexing the ions with organic chelants capable of holding both ferric and ferrous ions in solution.

During oxidation of hydrogen sulfide to elemental sulfur, the reaction reduces the ferric ($Fe^{3+}$) ion to the ferrous ($Fe^{2+}$) ion. The reactions are represented as follows:

$$H_2S + 2Fe^{3+} \rightarrow 2Fe^{2+} + 2H^+$$

$$2H^+ + 2Fe^{2+} + 1/2 O_2 \rightarrow 2Fe^{3+} + H_2O$$

The rate of $H_2S$ oxidation is a function of the pH, temperature, concentration of the $Fe^{3+}$ chelate, the gas/redox solution liquid ratio and the degree of agitation. When the sour gas stream is bubbled through the Virtis Omni-Culture Bioreactor containing the liquid catalyst, the hydrogen sulfide is completely reduced at a pH exceeding 6.0. As the sour gas stream is bubbled through the reactor, the ferric ions in the catalysts are reduced to ferrous ions. Regeneration was accomplished by bubbling (atmospheric) air through the liquid catalyst. A variety of liquid catalysts are suitable for oxidation of hydrogen sulfide. For example, non-chelated ferric sulfate, ferric ethylenediamine tetraacetate, ferric nitrilotriacetate, and the commercially chelated catalysts ARI 310 and ARI 340. The ARI 310 and 340 liquid catalysts are tradenames for commercial products sold by ARI Technologies of Palatine, Ill. or Wheelabrator Clean Air Technologies, Inc. The products ARI 310 and ARI 340 are also known as LO-CAT.

LO-CAT 310 and LO-CAT 340 catalysts were obtained from Wheelabrator Clean Air Technologies Inc. (formerly ARI Technologies Inc.) of Palatine, Ill. These catalysts contain chelated ferric ion complexes. The precipitation of ferric ions is prevented by chelating the ferric ions with organic chelates. The LO-CAT 310 and 340 are understood to comprise at least two constituent types of chelates: type A chelates, such as ethylenediaminetetraacetic acid (EDTA), nitrilotriacetic acid (NTA), or N-hydroxyethylenediaminetriacetic acid (HEDTA); and type B chelates, represented by polyhydroxylated sugars such as sorbitol. A combination of these two types of chelating agents are believed to promote stability of the catalyst over a broader range of pH than one type alone and for this reason are featured in commercial catalyst formulations designed for such uses, such as LO-CAT 310 and 340.

These two types of chelates are combined with a biostat (such as, for example, ARI-400) at a concentration of about 10 ppm to about 20 ppm in either LO-CAT solution in order to prevent the growth of undesirable bacteria in the processing units. All other chemicals used herein were obtained from Sigma Chemical Company.

Synthetic sour gas samples used in this study were blended by Alphagaz Inc. of LaPorte, Tex. The synthetic sour gas had the following composition:

$H_2S$—0.5 to 0.79% (v/v)

$CO_2$—5.0% (v/v)

$N_2$—94.21% to 94.5%

The pH of the catalyst solution was maintained between 7.0 to 8.0. The pH was measured using ORION 91 Series pH electrodes with Ag/AgCl internal reference systems. The pH meter was calibrated by single-buffer calibration (pH 4.0 buffer) prior to all the measurements. Separate pH probes were maintained for control solutions and the bacterial solutions to avoid contamination of the probes. The pH probes were stored in a solution containing 200 mL pH 7.0 buffer with 1 g KCl.

The redox potential is a relative measure of the electrically active iron (in the state of Ferric ions, $Fe^3$) available in the solution, and determines the oxidizing or reducing capability of the solution. The redox potential of the solution thus varies depending on the level of ionization at which the measurement was taken. Fresh redox solutions are characteristically highly oxidized and thus have the highest redox potential. The range of redox potentials and their significance are listed below:

| RANGE | DESCRIPTION |
|---|---|
| 0 to +150 mV | Highly oxidized |
| −250 to 0 mV | Normal |
| <−250 mV | Overreduced |

The redox potentials of the solutions were measured using a ORION MODEL 96-78 Platinum redox electrode with a Ag/AgCl reference electrode in one body.

Dissolved oxygen, a measure of biological oxygen demand (BOD), was measured in the LO-CAT solutions during the oxidation and regeneration cycles with an ORION MODEL 97-08 oxygen electrode. The electrode allows measurement of the dissolved oxygen directly in parts per million (ppm) on a pH meter.

Ferrous ion and total ion concentrations in the media and chelated catalyst solutions were determined by volumetric analysis and verified with atomic absorption spectroscopy. The ferric ion content was determined by the difference between ferrous ion and total iron concentration.

In the volumetric analysis, the samples were titrated against a standard, (0.025 N) potassium dichromate, with di-phenylamine sulfonate as the indicator. The end point was sharp and stable. A standard procedure for the estimation of total iron is described by Young. The total iron concentration was also determined using a Perkin-Elmer-3100 Atomic Absorption Spectrophotometer operated at 248.5 nm wavelength, 0.2 nm slit, 25 amp lamp current and 30 second reading cycle. The total iron concentration was estimated by the following relationship:

1 mL of 0.025 N $K_2Cr_2O_7$=0.001396 g Fe

The outlet $H_2S$ gas concentrations from the reactor during the oxidation cycle of the experiment was measured using a Tutweiler burette. A fixed volume of gas was taken into the Tutweiler apparatus and then titrated with 0.025 N iodine solution with starch as the indicator. The gas reacts with the iodine to form elemental sulfur and the end point of this reaction is reached when the color of the starch visibly turns blue. The reaction stoichiometry is as follows:

$$H_2S + I_2 \rightarrow S + 2I^- + 2H^-$$

This technique can be used for a wide range of $H_2S$ concentrations ranging form 0 to 50,000 ppm (0.0 to 5.0%). The concentration of $H_2S$ in the outlet gas was calculated according to the following equation:

$$\%H_2S(v/v) + \frac{V}{G} \times 22.4 \frac{T}{273} \times 100\%$$

Where
  V=vol. of $I_2$ consumed (mL)
  G=vol. of gas (100 mL)
  N=normality of $I_2$(eq/L)
  2=equivalents/mol $H_2S$
  22.4=volume of 1 mol. gas at STP
  T=gas temperature in degrees K
  273=gas temperature at STP (K)

Thiosulfate ($S_2O_3$) is a major by-product formed in the described liquid catalyst process. Although small concentrations of thiosulfate appear to promote the stability of the chelating agents in the catalyst solution, excessive thiosulfate production apparently leads to high caustic consumption and salt buildup which results in plugging of the spargers. Higher thiosulfate buildup leads to increase the specific gravity of the solution which results in increased blowdown and hence increased catalyst consumption.

To titrate, the thiosulfate containing sample is added to a known excess of iodine solution. Two moles of thiosulfate react with one mole of iodine as follows:

$$2S_2O_3 = +I_2 \rightarrow 2I^- + S_4O_6^-$$

The excess iodine is then back titrated with standard thiosulfate solution. The amount of iodine reacted with the thiosulfate present in the sample is obtained by the difference. Starch, which is used as a indicator, forms a blue color with iodine. The end point is observed when the blue color of the starch-iodine complex disappears. The amount of thiosulfate present in the sample is calculated using the following equation:

$$S_2O_3^-(g/l) = \frac{(B - A) \times N \times 112}{S}$$

Figure 3A:
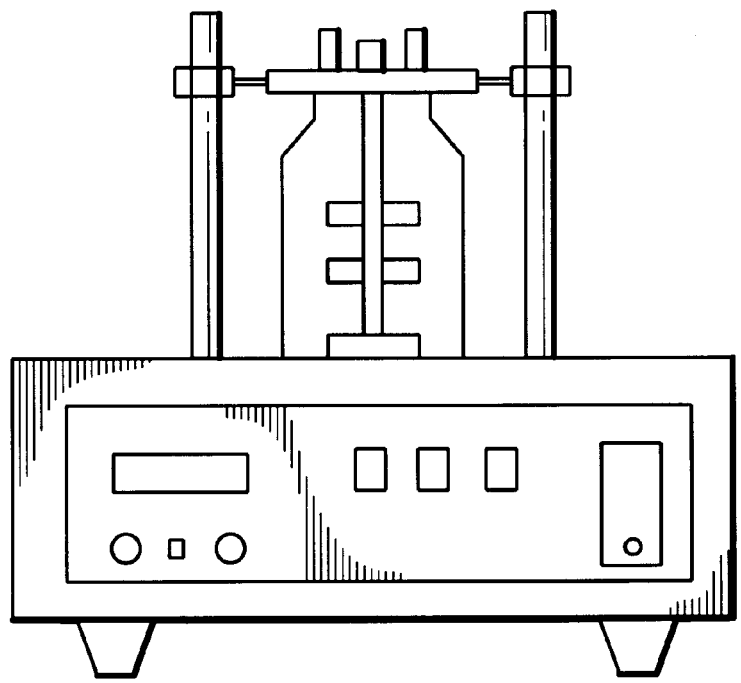
FIG. 3 is a schematic diagram of the Virtis Omni-Culture Bioreactor.
Figure 3B:
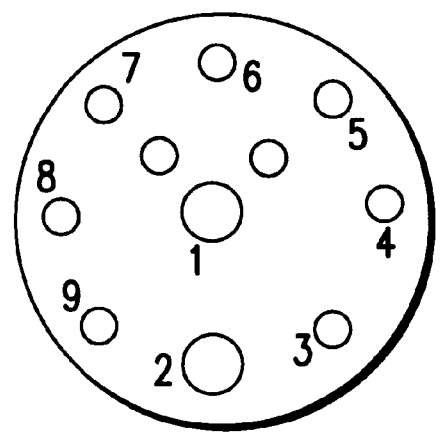
Figure 4:
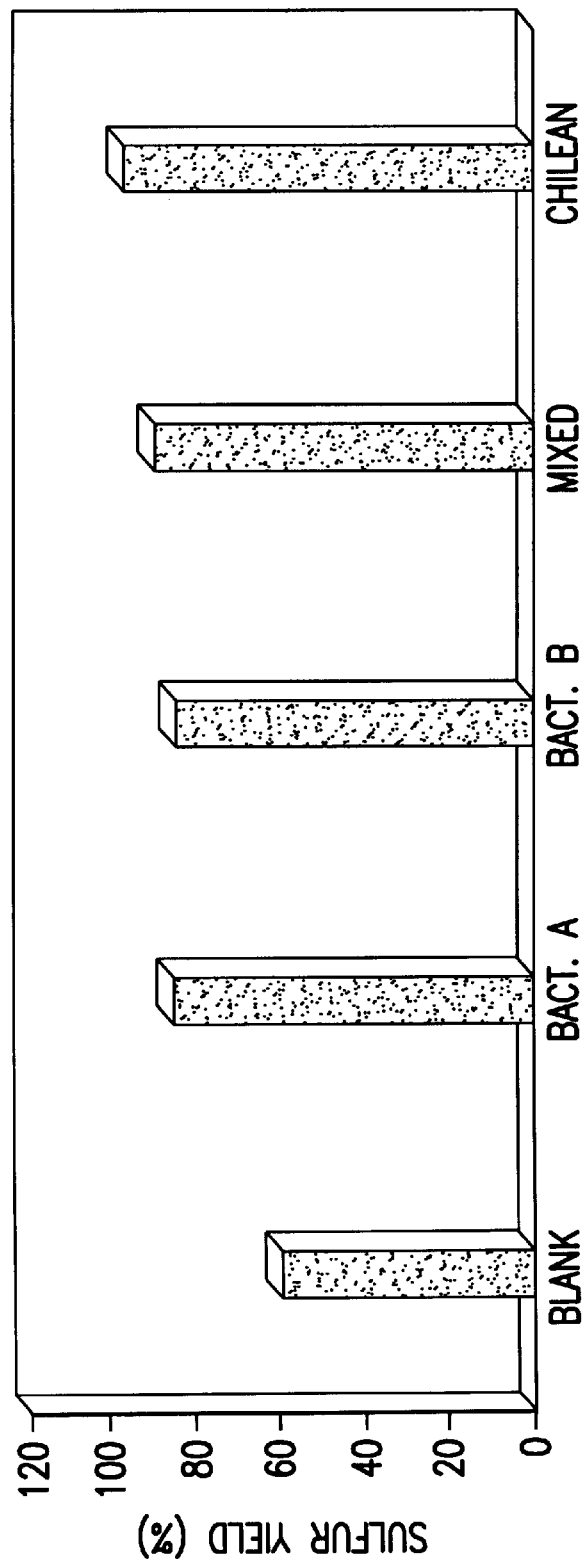
FIG. 4 is a graph illustrating the effect of bacterial cultures (A, B, Mixed and Chilean) under experimental conditions (50° C., pH 8.5) on sulfur recovery (percent of theoretical) in the redox system ARI-340 and compares with blank (absence of bacteria) experiment.
Figure 5:
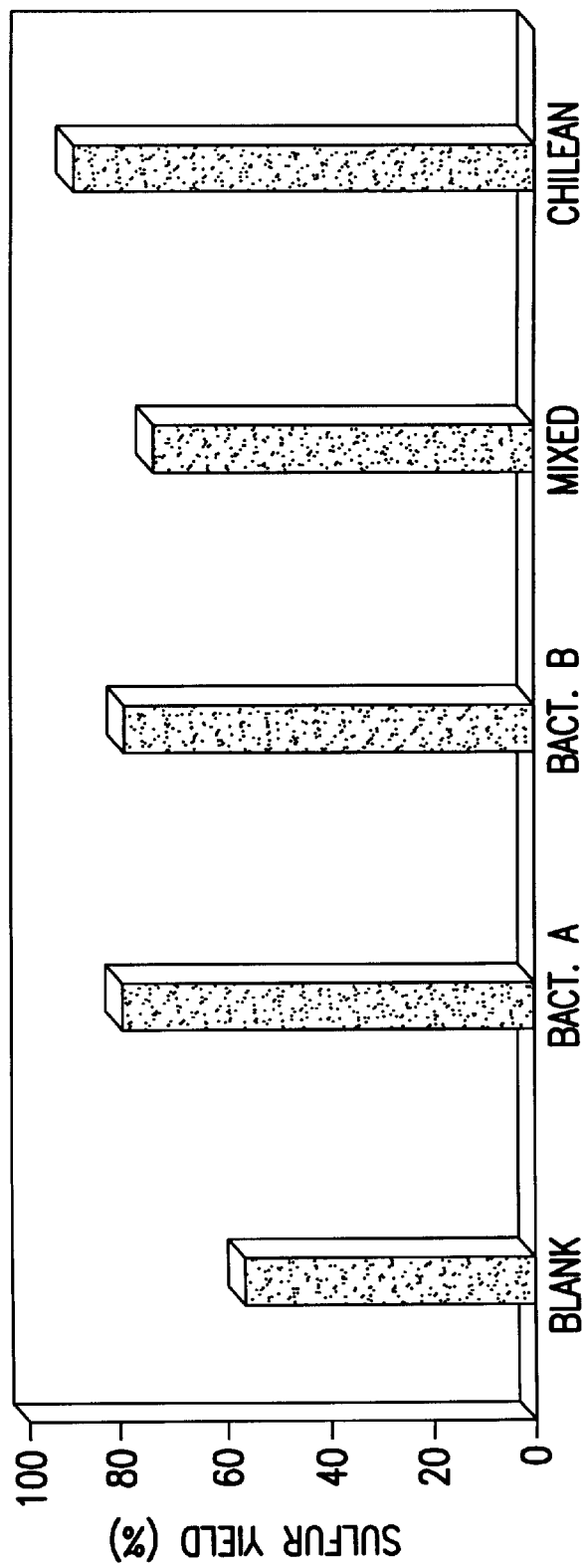
FIG. 5 is a graph illustrating the effect of bacterial cultures (A,B, Mixed and Chilean) under experimental conditions (40° C., pH 8.5) on sulfur recovery (percent of theoretical) in the redox system using ARI-340 catalyst and compares with blank (absence of bacteria) experiment.
Figure 6:
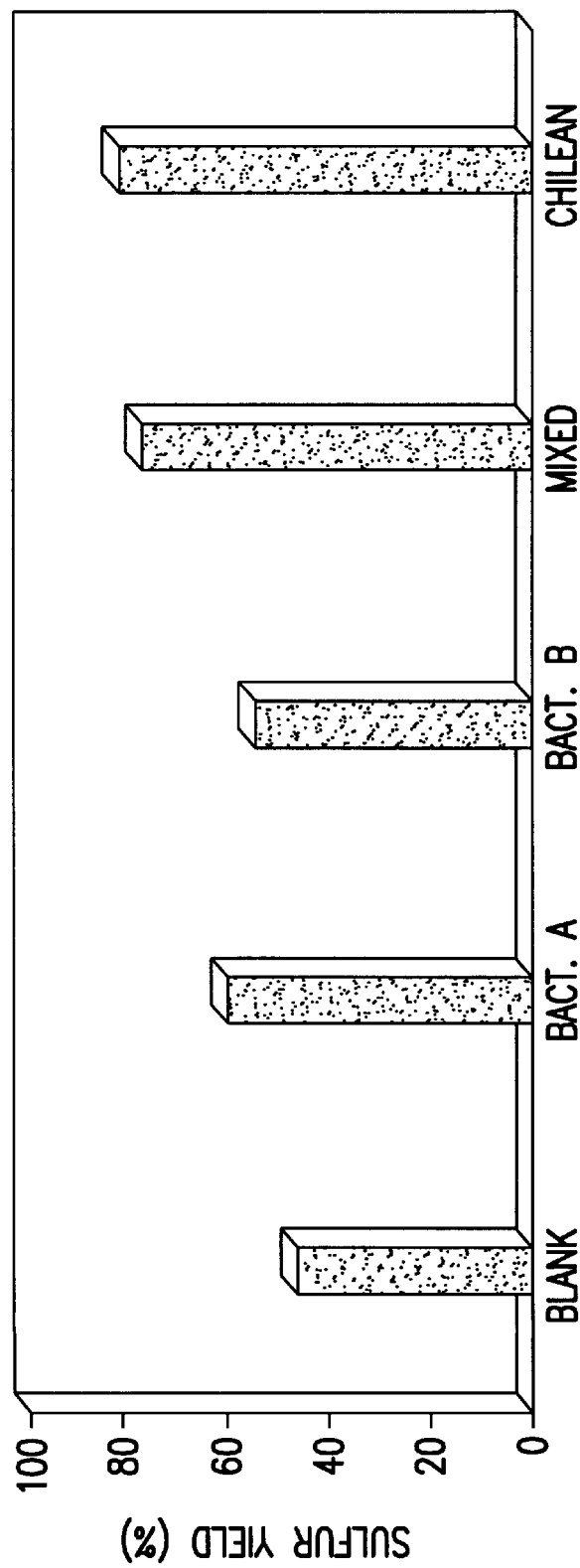
FIG. 6 is a graph illustrating the effect of bacterial cultures (A, B, Mixed and Chilean) under experimental conditions (30° C., pH 8.5) on sulfur recovery (percent of theoretical) in the redox system using ARI-340 catalyst and compares with blank (absence of bacteria) experiment.
Figure 7:
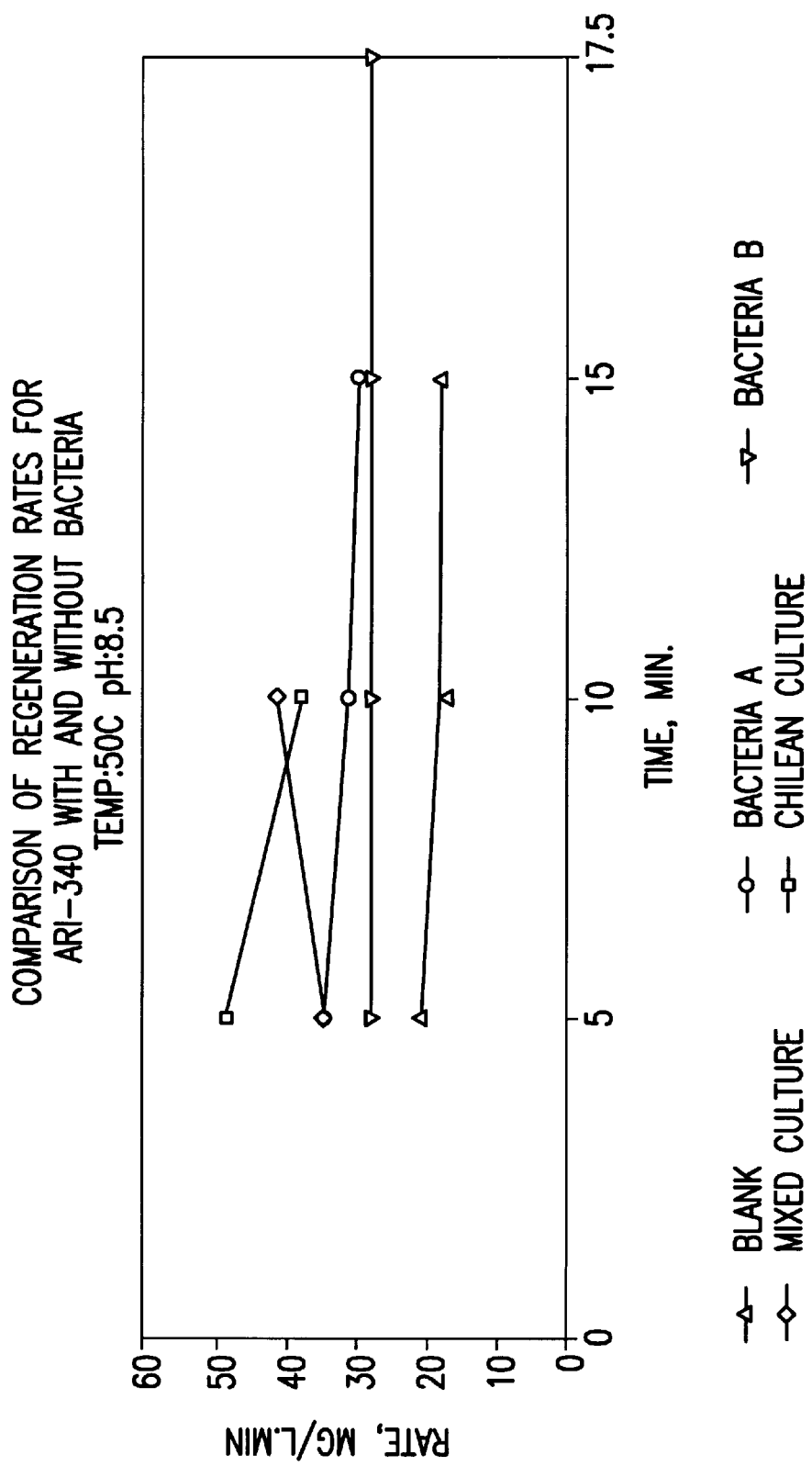
FIG. 7 is a graph illustrating the effect of bacterial cultures (A, B, Mixed and Chilean) under experimental conditions (50° C., pH 8.5) on ferric ion regeneration rates (mg/L. min) as a function of time in the redox system using ARI-340 catalyst and compares with blank (absence of bacteria) experiment.
Figure 8:
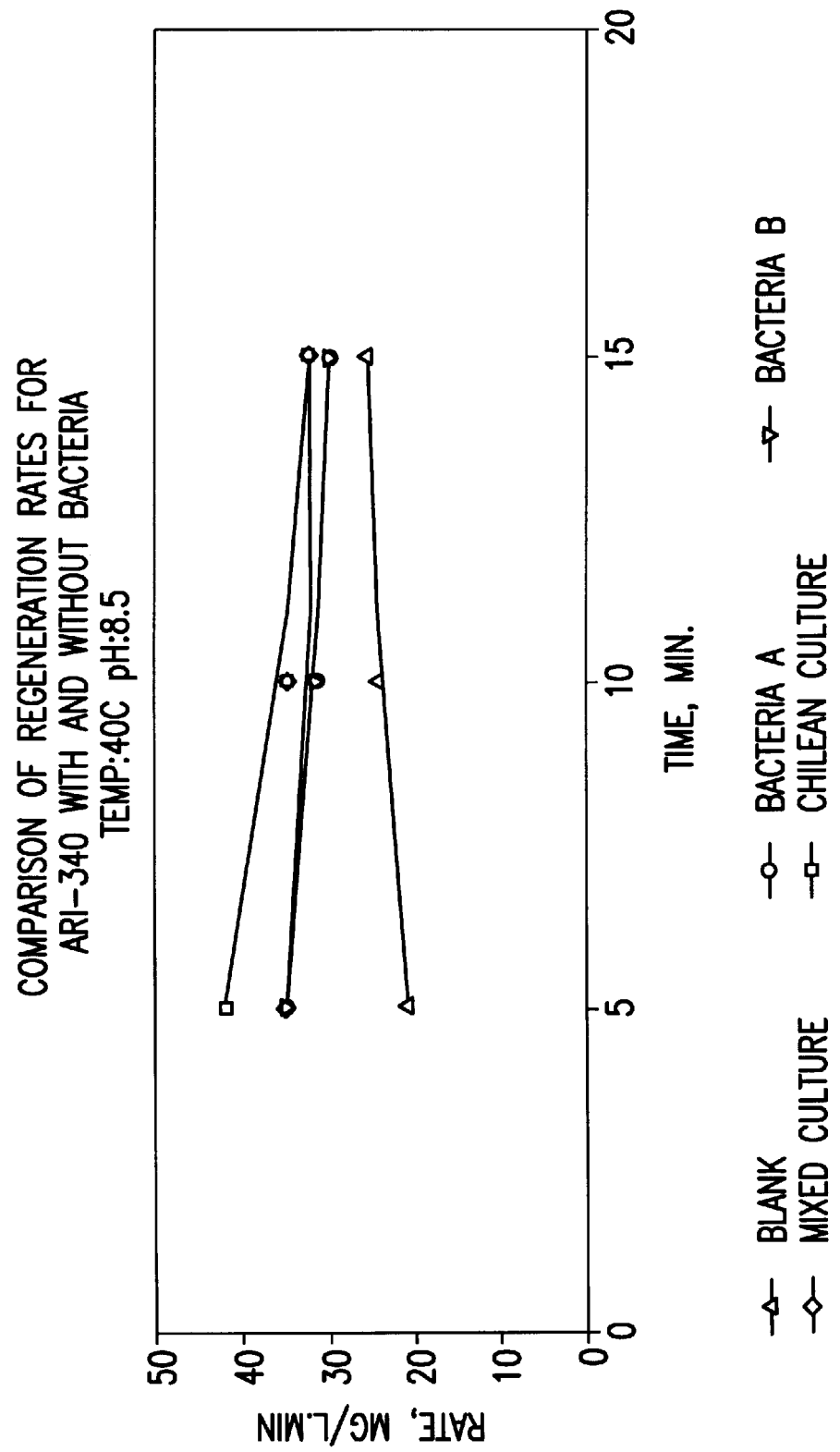
FIG. 8 is a graph illustrating the effect of bacterial cultures (A, B, Mixed and Chilean) under experimental conditions (40° C., pH 8.5) on ferric ion regeneration rates (mg/L. min) as a function of time in the redox system using ARI-340 catalyst and compares with blank (absence of bacteria) experiment.
Figure 9:
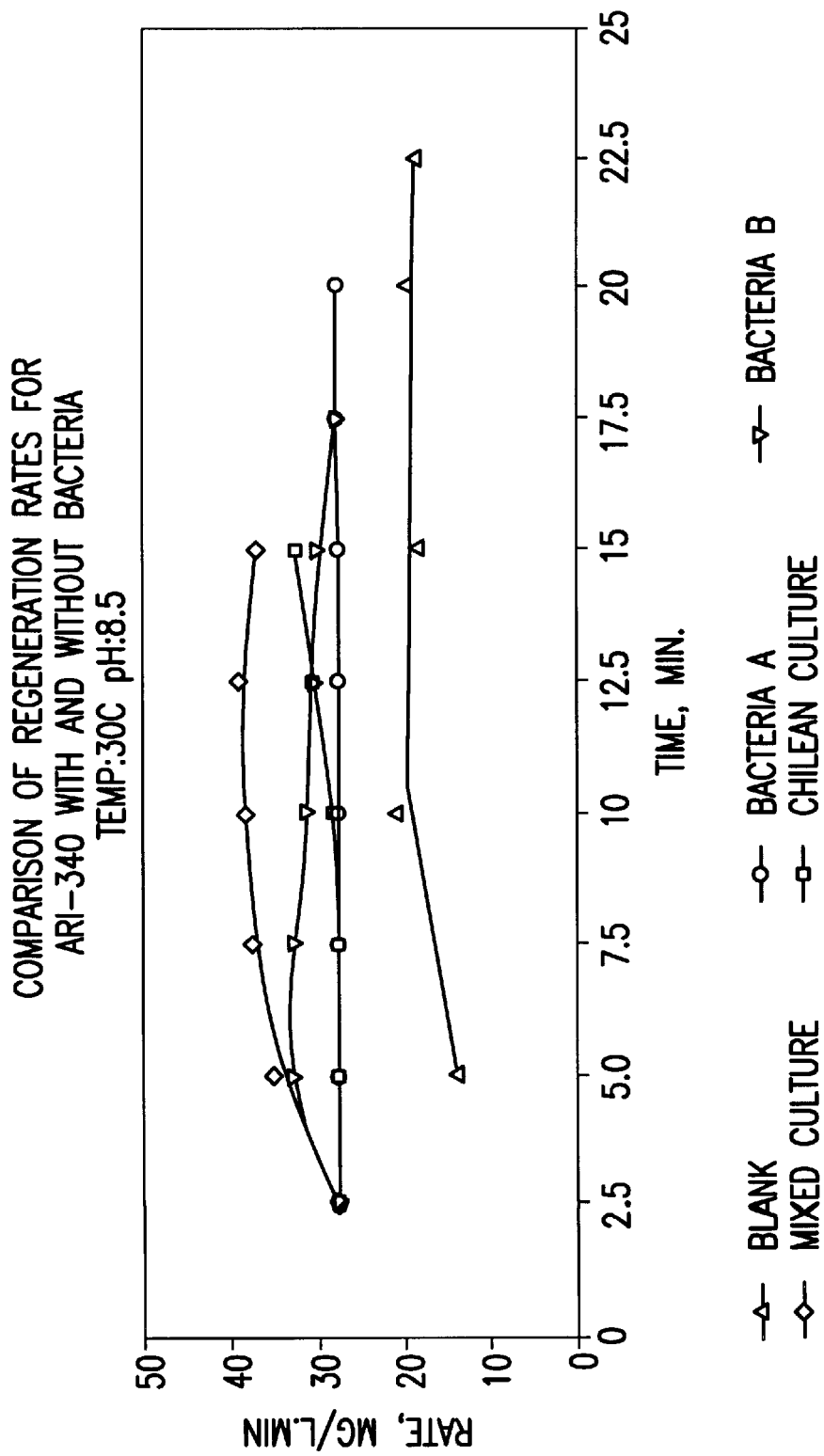
FIG. 9 is a graph illustrating the effect of bacterial cultures (A, B, Mixed and Chilean) under experimental conditions (30° C., pH 8.5) on ferric ion regeneration rates (mg/L. min) as a function of time in the redox system using ARI-340 catalyst and compares with blank (absence of bacteria) experiment.

Where
  A=vol. of titrant used in sample titration (mL)
  B=vol. of titrant used in blank titration (mL)
  N=normality of sodium thiosulfate solution (eq/L)
  S=vol. of sample used (mL) &
  112=formulate wt. of thiosulfate radical A schematic layout of the two liter Virtis Omni-Culture Bioreactor used in the oxidation of $H_2S$ is shown in FIG. 3. This bioreactor comprises a temperature sensor with a heating element and a compressed air supply unit, and a magnetic agitator. The stirring rate can be varied up to 600 rpm. Typically, however, the experiments were carried out at 300 rpm. The reactor vessel and the agitator were autoclaved at 270° F. and 20 psig(?) for 15 minutes prior to each cycle to avoid contamination of the catalyst solutions.

Batch runs were initially carried out at two different temperatures, at 25° C. and at 30° C., respectively, at pre-optimized: pH, total iron concentration, hydrogen sulfide flow and air flow rates. In the first batch step, hydrogen sulfide from the synthetic sour gas blend was passed (sparged) through the chelated iron catalysts, wherein the ferric ion ($Fe^{3+}$) is reduced to ferrous ion ($Fe^{2+}$) and hydrogen sulfide is oxidized to elemental sulfur. In the second batch step, the solution was regenerated by sparging air through the reduced redox solution under controlled experimental conditions. The elemental sulfur produced was removed in some cases by filtration alone or with centrifugation, after which it was dried and weighed.

The rate of hydrogen sulfide oxidation is a function of the pH, temperature, concentration of $Fe^{3+}$ chelate, the gas/liquid ratio, and the degree of agitation. These variables were carefully controlled and have been optimized as disclosed. Similarly, the rate of ferric ion regeneration is a function of the pH of the redox solution, the temperature, concentration of the chelated iron, air to liquid ratio and the degree of agitation. The progress of the reaction was monitored by measuring the concentration of $Fe^{2+}$, $Fe^{3+}$, pH, temperature, redox potential of the reaction mixture in the reactor, all as disclosed herein.

Cell densities ranging from 1.0 to $2.0 \times 10^{11}$ cells/L were achieved in the redox system solutions. Cell densities of 1.0 to $1.5 \times 10^9$ cells/L were used in experiments carried out in the presence of the bacteria.

A set of one cycle experiments using one liter solutions of the commercial iron chelate catalysts, LO-CAT 310 and LO-CAT 340, at a total iron concentration of 1000 ppm were carried out in the absence of *Thiobacillus ferrooxidans* -23270(baseline) at pH of 7.5, and a $H_2S$ gas flow rate of 0.0005 scf/s. The commercial chelated catalysts were: LO-CAT 310 and LO-CAT 340. In the oxidation cycle, hydrogen sulfide gas was sparged through the catalyst solution in the Virtis Omni-Culture Bioreactor for 30 minutes. The temperature and the agitation speed were set at 25° C. and 300 rpm respectively. The ferrous and ferric ion, and the outlet hydrogen sulfide gas concentrations were determined at ten minute intervals. At the end of 30 minutes, dissolved oxygen was determined and the pH was adjusted to 7.5 by the addition of 10N NaOH or 1N $H_2SO_4$. The reduced catalyst solution was regenerated by sparging air at a rate of 0.0016 scf/s.

During oxidation of hydrogen sulfide to elemental sulfur, the reaction reduces the ferric ($Fe^{3+}$) ion to the ferrous ($Fe^{2+}$) ion. The reactions are represented as follows:

$$H_2S + 2Fe^{3+} \rightarrow 2Fe^{2+} + 2H^+$$

$$2H^+ + 2Fe^{2+} + 1/2O_2 \rightarrow 2Fe^{3+} + H_2O$$

The rate of $H_2S$ oxidation is a function of the pH, temperature, concentration of the $Fe^{3+}$ chelate, the gas/redox solution liquid ratio and the degree of agitation. When the sour gas stream is sparged through the Virtis Omni-Culture Bioreactor containing the liquid catalyst, the hydrogen sulfide is completely reduced at a pH exceeding 6.0. As the sour gas stream is bubbled through the reactor, the ferric ions in the catalysts are reduced to ferrous ions. Regeneration was accomplished by bubbling air through the liquid catalyst. A variety of liquid catalysts are suitable for the described oxidation of hydrogen sulfide, such as alone or in non-chelated ferric sulfate, ferric ethylenediamine tetraacetate, ferric nitrilotriacetate, commercially chelated catalysts ARI 310 or ARI 340.

Regeneration by sparging air through the liquid catalyst occurred in 20 minutes with a 1% ARI 310 iron concentration level, in 40 minutes with a 5% ARI 310 iron concentration level, and in 80 minutes with 10% ARI 310 iron concentration levels.

Naturally occurring Chilean cultures of iron oxidizing bacteria were also used to regenerate the commercially used iron chelates for reoxidation of reduced redox solutions. The Chilean cultures used in this study were maintained in basal salt solution at a low pH prior to their use. The bacteria were grown in 9K media and maintained at 25° to 45° C. in a controlled shaker bath. The composition of the media is shown in Table 1. The maximum cell growth typically occurred in 25 to 50 hours resulting in a cell density of $1.5 \times 10^{10}$ cells/1 in 9K media. Bacterial cell counts were determined using a Petroff bacteria counter under a phase contrast microscope. The gas samples and catalysts used, were those described in the foregoing reactions. Two sets of experiments were conducted in each case, one in the absence of bacteria (blank) and the other one in the presence of a single bacteria, or a mixed culture such as Chilean culture.

The iron oxidizing bacteria were maintained in basal salt solutions at a low pH prior to their use. One bacteria, *Thiobacillus ferrooxidans* ("A"), was grown in 9K media and the other bacteria, *Laptospirillum ferrooxidlans* ("B"), was grown in a high pH nutrient media. These bacteria were also grown in a redox solution system for three to five days prior to use in a high pH media maintained at 25° to 45° C. in a controlled temperature shaker bath. The iron oxidizing bacterial mixed cultures used in this study were initially obtained from American Type Culture Collection (ATCC), however, they were cultivated either in a high pH media or grown in the redox solution used for the hydrogen sulfide oxidation studies. The cultures were grown separately and then mixed and also were grown in the same media. The maximum cell growth typically occurred in 25 to 50 hours resulting in a cell density of $1.5 \times 10^{11}$ cells/1 in high pH media. The cell densities of 1.0 to $2.0 \times 10^{11}$ cells/1 were achieved in the redox system solutions. Cell densities of $(1.0–1.5) \times 10^9$ cells/1 were used.

1. One-Cycle Experiment Using Commercial Chelated Catalysts

A set of experiments was conducted at 30° to 50° C. and pH varying from 5, 7.5 and 8.5 using 1000 ppm solution of commercial iron-chelate ARI-340 in absence of iron oxidizing bacteria (baseline). A cycle comprises the steps of: (a) oxidation of hydrogen sulfide by bubbling it through redox solution, (b) filtration of elemental sulfur followed by (c) reoxidation of ferrous ions with air. In a typical experiment, hydrogen sulfide was oxidized by passing the synthetic sour gas mixture through one liter of redox solution in Virtis Omni-Culture Bioreactor, elemental sulfur was vacuum filtered and the redox solution was reoxidized to ferric ions by bubbling air. The redox solution regeneration rates were fairly constant, for a specific pH, temperature and gas to liquid ratio in the control (baseline) experiments and the quantity of the elemental sulfur recovered ranged from 40 to 55% of the theoretical amount.

2. One-Cycle Experiment Using ARI-340 in Presence of Iron Oxidizing Bacteria Experiments were conducted at 30° C. to 50° C. and pH varying from 5, 7.5 and 8.5 using 1000 ppm solution of commercial iron-chelate ARI 340 in the presence of the Chilean culture. As above, a cycle comprises the steps of: (a) oxidation of hydrogen sulfide by bubbling through redox solution, (b) vacuum filtration of elemental sulfur followed by (c) reoxidation of ferrous ions with air in the presence of the Chilean culture. The redox solution was reoxidized to ferric ions by bubbling air in the presence of the Chilean culture at a cell concentration of $1.0 \times 10^9$ to $2.5 \times 10^{10}$ cells/liter. The data on these experiments is shown in FIGS. 4–9 and is compared with the baseline experimental data obtained in absence of bacteria. The data shows that the redox solution regeneration rates were enhanced from 80 to 200% and an increase in the quantity of the elemental sulfur recovered ranged from 85% to 99% of the theoretical amount as compared to 40 to 55% in the absence of bacteria.

Thermal Stability Experiments

The thermal stability of *T. ferrooxidans* in redox solutions, LO-CAT 310 and LO-CAT 340 was investigated at temperatures ranging from ambient up to 50° C.

1. Thermal Stability of *T. ferrooxidans* in Redox Solutions Using LO-CAT 310 at 30° C.

Two sets of samples containing 1010 ppm of total iron in LO-CAT 310 were incubated at 30° C. and an initial pH of 7.7 for ten days. The $Fe^{2+}$, $Fe^{3+}$ concentrations, pH, and redox potential were monitored daily for the control sample without bacteria and $Fe^{2+}$, $Fe^{3+}$, pH, redox potential and *T. ferrooxidans* 23270 cell density were monitored for the sample inoculated with *T. ferrooxidans* 23270 cells containing $1.6 \times 10^{11}$ cells/L.

Figure 10:
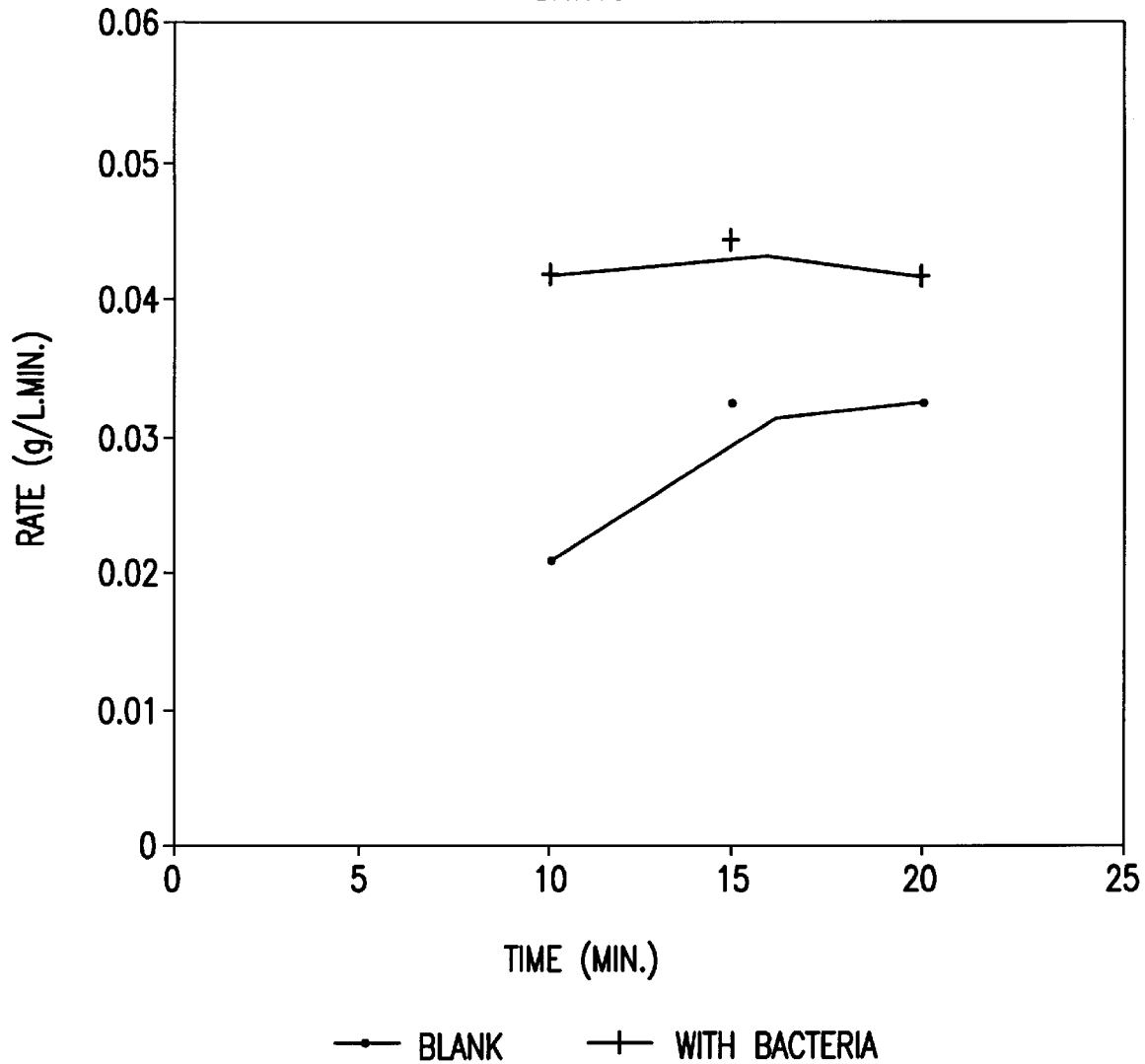
FIG. 10 is a graph illustrating the effect of *Thiobacillus ferrooxidans* culture incubated in ARI-3 10 solution at 30° C. for 10 days and evaluated for it ferric ion regeneration rate (mg/L.min) at 25° C., pH 8.5 as a function of time in the ARI-3 10 redox system and compares with blank (absence of bacteria) experiment.
Figure 11:
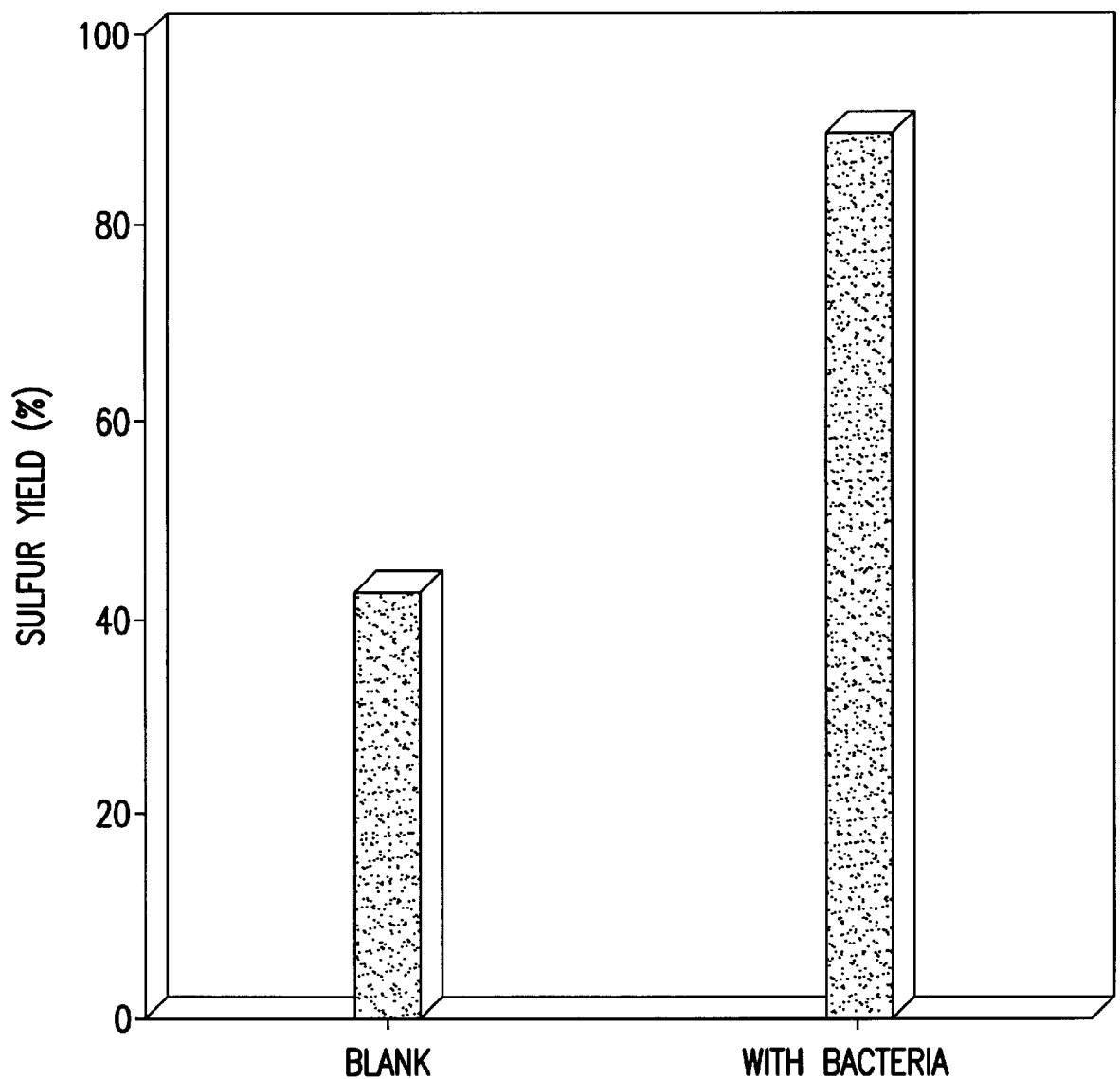
FIG. 11 is a graph illustrating the effect of *Thiobacillus ferrooxidans* culture incubated in ARI-310 solution at 30° C. for 10 days and evaluated for its sulfur recovery capability (percent of theoretical) at 25° C. and pH 8.5 in ARI-3 10 redox system and compares with blank (absence of bacteria) experiment.

After ten day incubation period, the LO-CAT 310 (baseline) and the LO-CAT 310 containing *T. ferrooxidans* 23270 were used for oxidation of $H_2S$ and subsequent re-oxidation of the reduced LO-CAT 310. FIGS. 10 and 11 compare the re-oxidation rates and variation in sulfur recovered respectively.

2. Thermal Stability of *T. ferrooxidans* in Redox Solutions Using LO-CAT 340 at 30° C.

Two sets of samples containing 837.6 ppm of total iron in LO-CAT 340 were incubated at 30° C. and an initial pH of 7.7 for ten days. The $Fe^{2+}$, $Fe^{3+}$ concentrations, pH and redox potential were monitored daily for the control sample without bacteria (baseline) and $Fe^{2+}$, $Fe^{3+}$, pH, redox potential and *T. ferroxidans* cell density were monitored for the samples containing the bacteria. The bacterial samples were inoculated with *T. ferrooxidans* 23270 at $1.2 \times 10^{11}$ cells/L.

Figure 12:
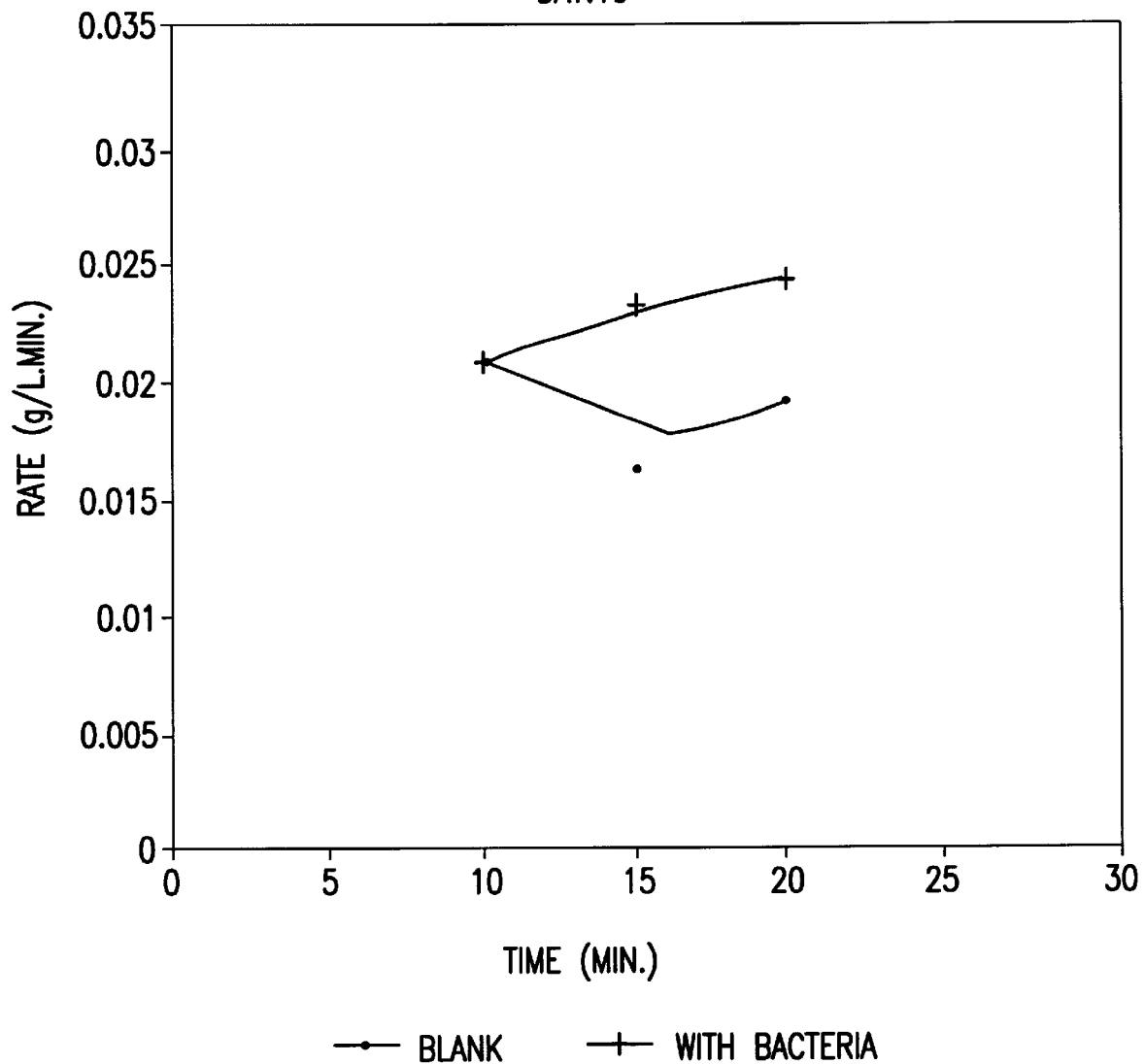
FIG. 12 is a graph illustrating the effect of *Thiobacillus ferrooxidans* culture incubated in ARI-340 solution at 30° C. for 10 days and evaluated for its ferric ion regeneration rate (mg/L. min) at 25° C. and pH 8.5 as a function of time in ARI-340 redox system and compares with blank (absence of bacteria) experiment.
Figure 13:
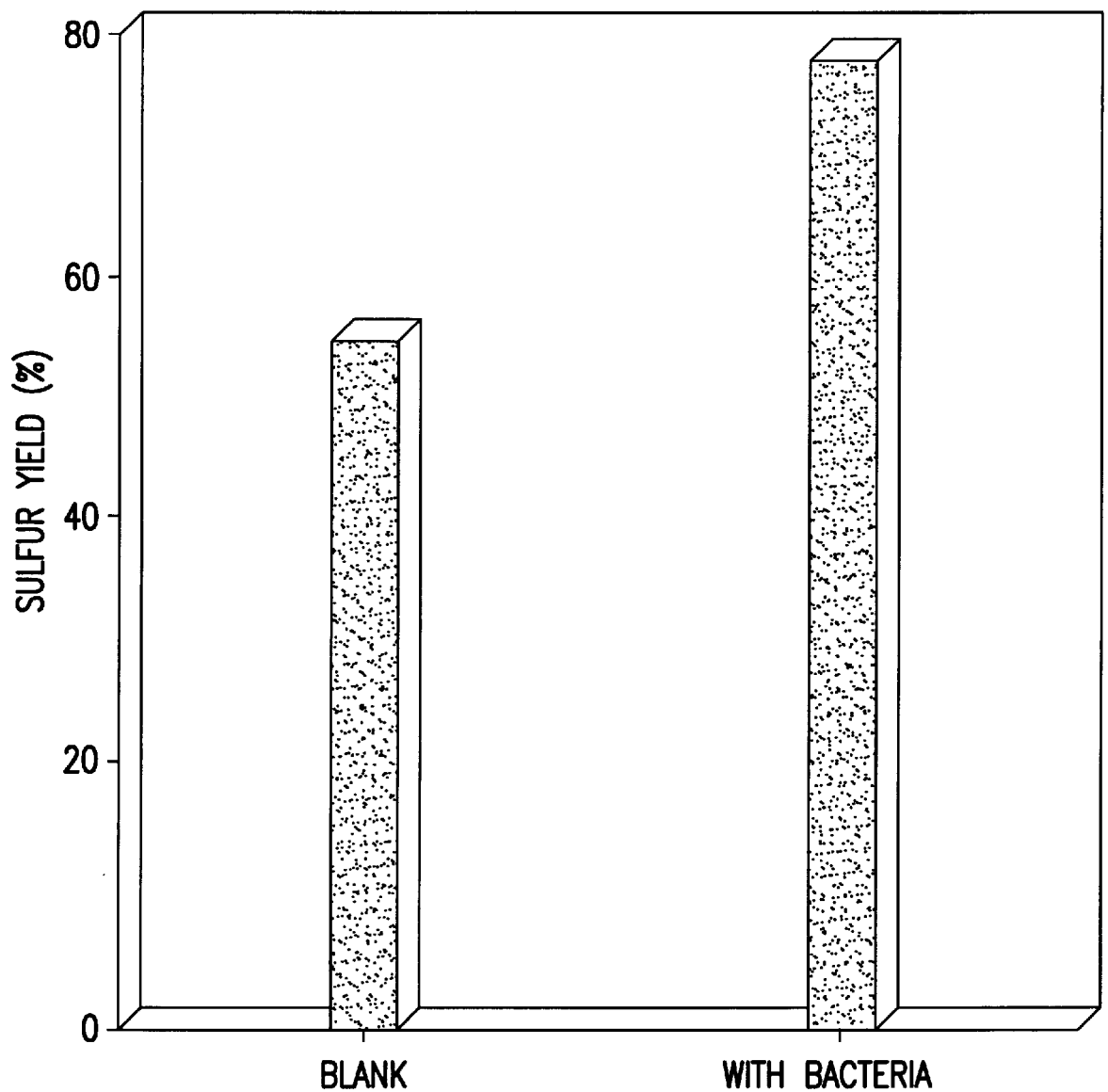
FIG. 13 is a graph illustrating the effect of *Thiobacillus ferrooxidans* culture incubated at 30° C. in ARI-340 solution for 10 days and evaluated for its sulfur recovery capability (percent of theoretical) at 25° C. and pH 8.5 in ARI-340 redox system and compares with blank (absence of bacteria) experiment.
Figure 14:
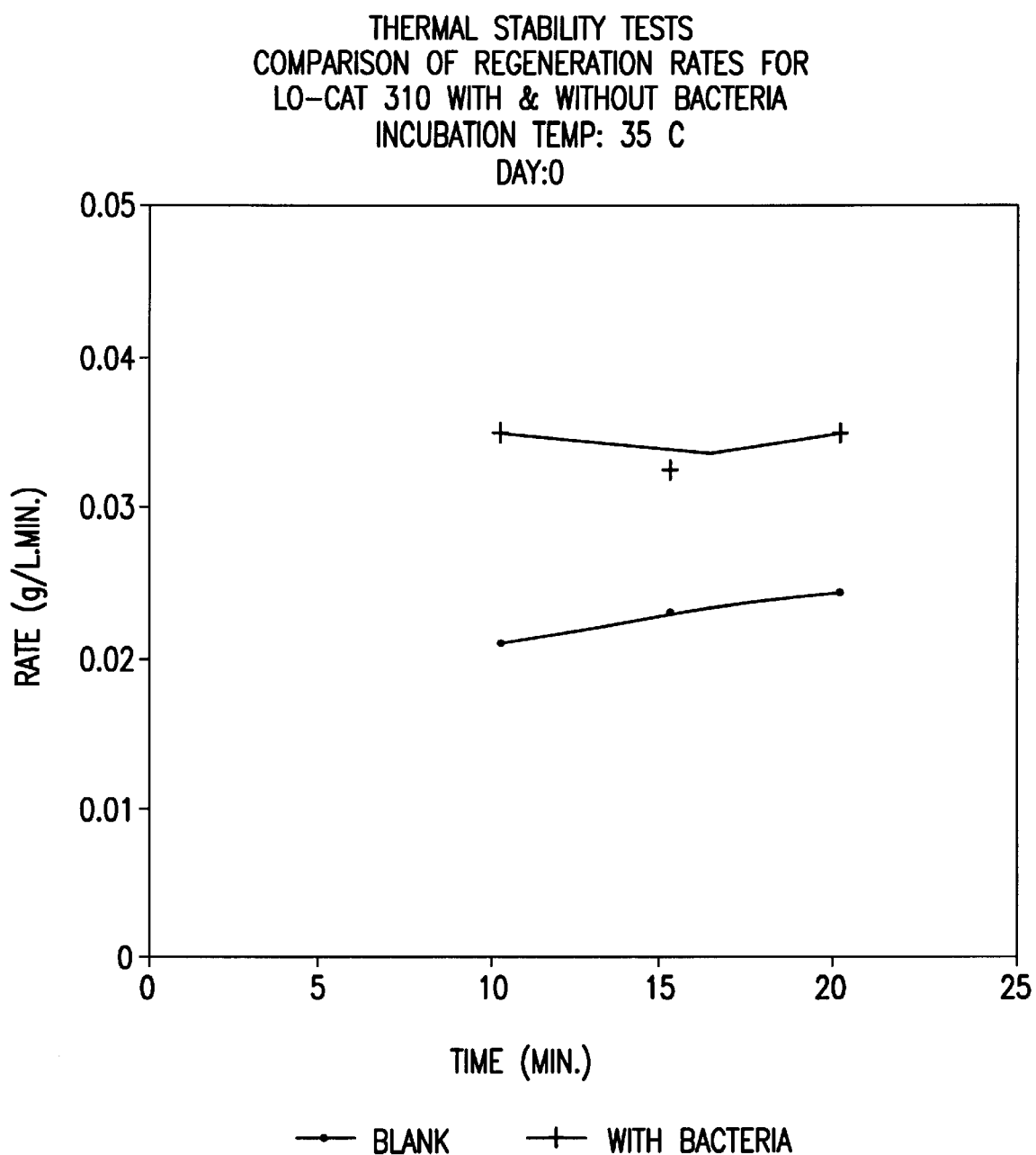
FIG. 14 is a graph illustrating the effect of *Thiobacillus ferrooxidans* culture incubated in ARI-3 10 solution at 35° C. for zero days and evaluated for its ferric ion regeneration rate (mg/L. min) at 25° C. and pH 8.5 as a function of time in ARI-310 redox system and compares with blank (absence of bacteria) experiment.
Figure 15:
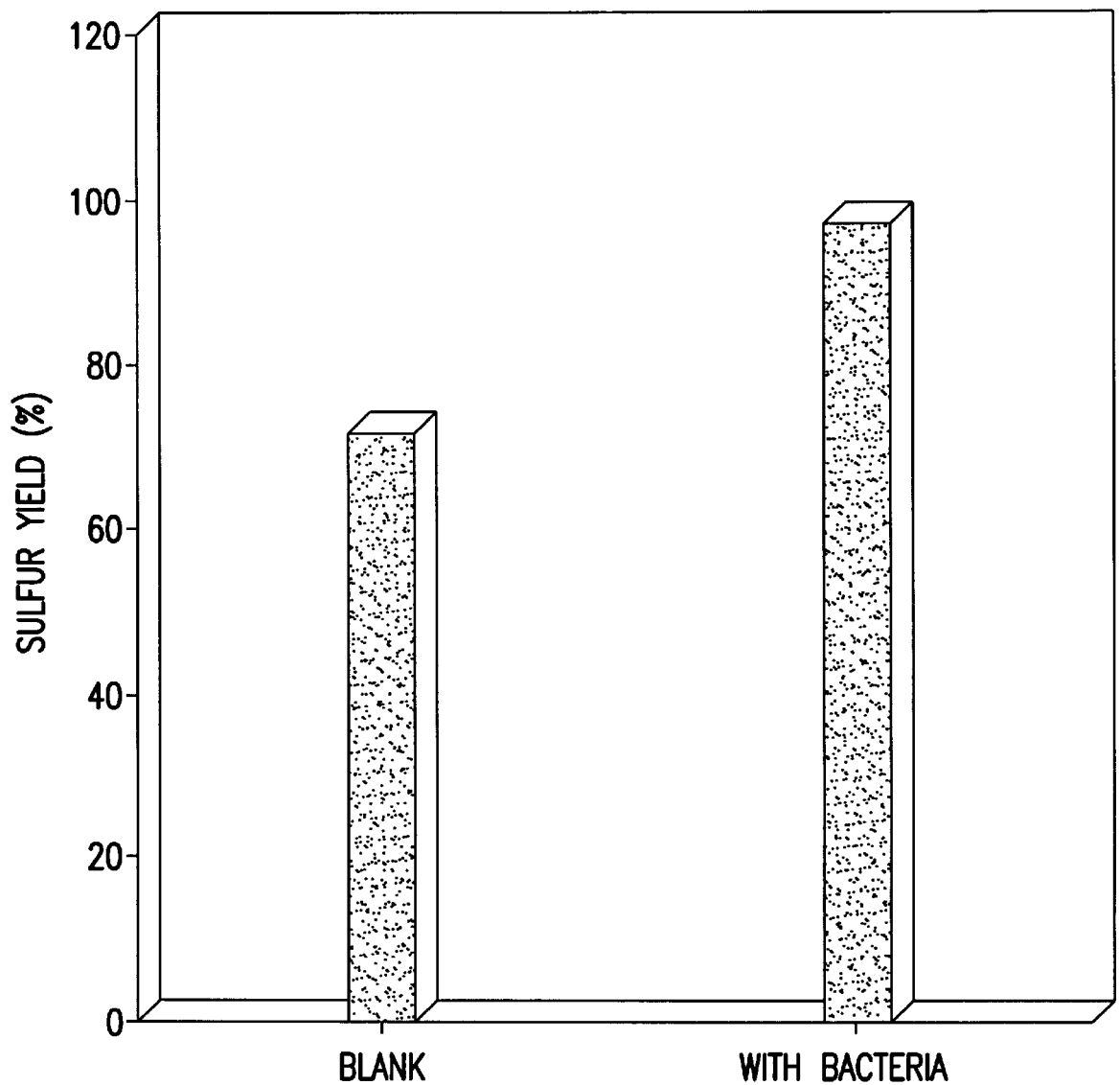
FIG. 15 is a graph illustrating the effect of *Thiobacillus ferrooxidans* culture incubated in ARI-310 solution at 35° C. for zero days and evaluated for its sulfur recovery capability (percent of theoretical) at 25° C. and pH 8.5 in ARI-310 redox system and compares with blank (absence of bacteria) experiment.
Figure 16:
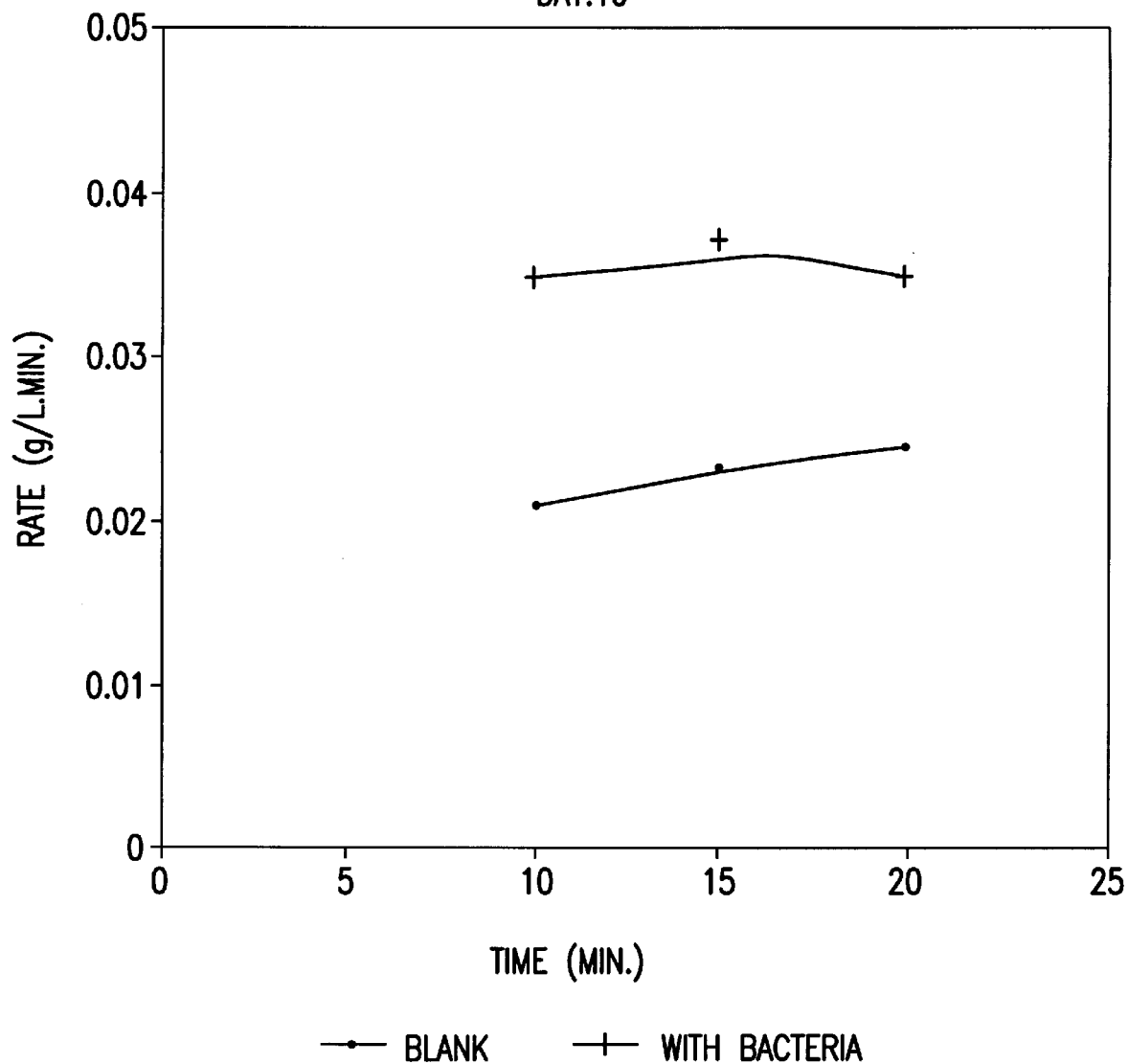
FIG. 16 is a graph illustrating the effect of *Thiobacillus ferrooxidans* culture incubated in ARI-310 solution at 35° C. for 10 days and evaluated for its ferric ion regeneration rate (mg/L. min) at 25° C. and pH 8.5, as a function of time in ARI-310 redox system and compares with blank (absence of bacteria) experiment.
Figure 17:
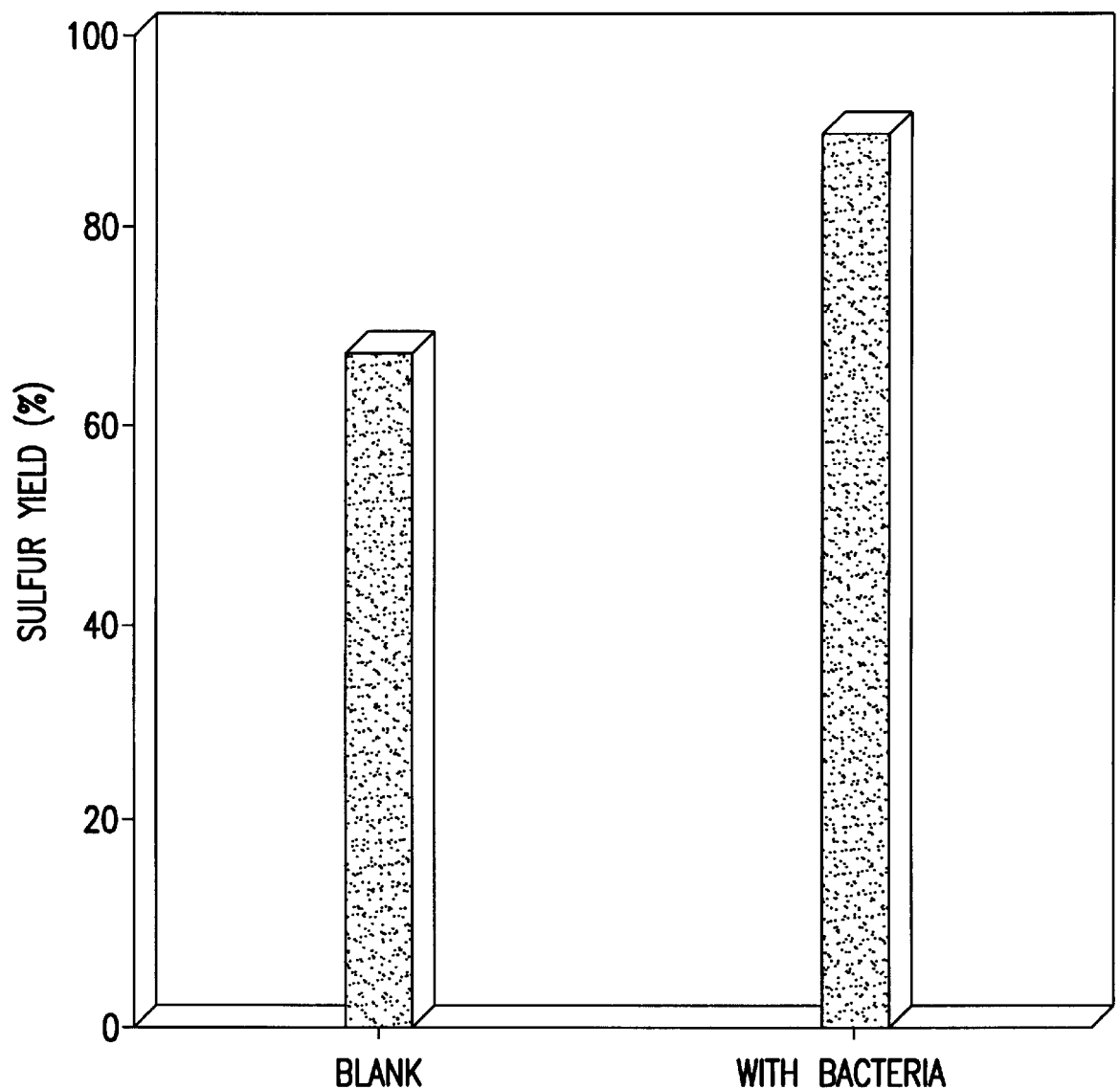
FIG. 17 is a graph illustrating the effect of *Thiobacillus ferrooxidans* culture incubated in ARI-310 solution at 35° C. for 10 days and evaluated for its sulfur recovery capability (percent of theoretical) at 25° C. and pH 8.5, ARI-310 redox system and compares with blank (absence of bacteria) experiment.

The samples incubated for ten days containing LO-CAT 340 without bacteria (blank) and with *T. ferrooxidans* were used for oxidation of hydrogen sulfide and subsequent reoxidation of the reduced LO-CAT 340 to the ferric state. FIG. 12 compares the regeneration rates for LO-CAT 340, and FIG. 13 compares the elemental sulfur recovery with and without *T. ferrooxidans* cells.

3. Thermal Degradation Studies with LO-CAT 310 and LO-CAT 340 in Presence of *Thiobacillus ferrooxidans* at 30° C.

Six samples of LO-CAT 310 without *T. ferrooxidans* (blank) and with *T. ferrooxidans* incubated at 30° C. and sampled at 0, 5 and 10-day intervals were blanketed with nitrogen and studied. Another set of six samples of LO-CAT 340 without *T. ferrooxidans* (blank) and with *T. ferrooxidans* incubated at 30° C. and sampled at 0, 5 and 10-day intervals were blanketed with nitrogen and studied.

Analysis of these samples for type A and type B chelates in LO-CAT 310 samples and for type A and type AB chelates in LO-CAT 340 samples indicate that type B chelate used in LO-CAT 310 samples in presence of *T. ferrooxidans* cells was used up by the bacterial cells. However, the effectiveness of LO-CAT 310 for $H_2S$ oxidation and the enhanced ferric ion regeneration rates were not affected during the ten-day test period.

The thermal stability test data with LO-CAT 340 containing Type A chelates, as well as Type AB chelates with and without *T. ferrooxidans* cells were not affected during the ten-day test period. The enhanced reoxidation rates as well as the increased sulfur recoveries in presence of *T. ferrooxidans* cells were not influenced.

4. Thermal Stability of *T. ferrooxidans* in Redox Solutions Using LO-CAT 310 at 35° C.

Two sets of samples containing 907 ppm of total iron in LO-CAT 310 were incubated at 35° C. and an initial pH of 7.7 for ten days. The $Fe^{2+}$, $Fe^{3+}$, pH and redox potentials were monitored daily for the control (blank) samples and in addition the *T. ferrooxidans* cell density for the samples inoculated with bacteria at a cell density of $1.0 \times 10^{11}$ cells/L.

At zero and ten-day incubation periods, both the control and the bacterial samples were subjected to one cycle experiments. Oxidation of hydrogen sulfide was carried out followed by reoxidation of the reduced LO-CAT 310 to the ferric state. FIGS. 14, 15, 16, and 17 compare the reoxidation rates and the sulfur recovered respectively for the control and the bacterial incubated samples.

5. Thermal Stability of *T. ferrooxidans* in Redox Solutions Using LO-CAT 340 at 35° C.

Two sets of samples containing 1033 ppm of total iron in LO-CAT 340 were incubated at 35° C. and an initial pH of 7.7 and kept in an incubator for ten days. The $Fe^{2+}$, $Fe^{2+}$, pH and redox potentials were monitored daily for the control (blank) samples without bacteria and in addition the *T. ferrooxidans* cell density was monitored for the samples containing bacteria at a cell density of $1.0 \times 10^{11}$ cells/L.

Figure 18:
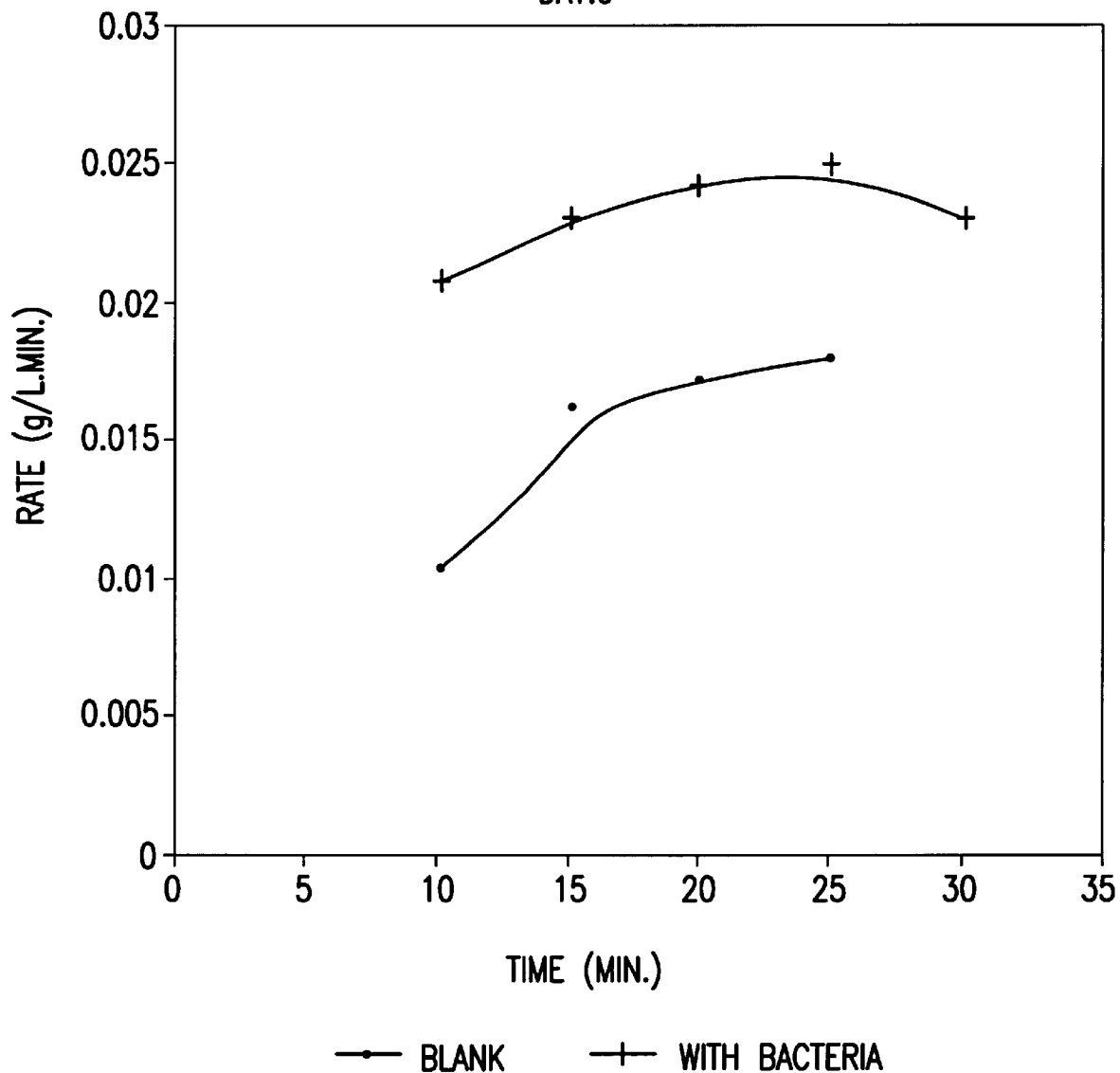
FIG. 18 is a graph illustrating the effect of *Thiobacillus ferrooxidans* culture incubated in ARI-340 solution at 35° C. for zero days and evaluated for its ferric ion regeneration rates (mg/L. min) at 25° C. and pH 8.5, as a function of time in ARI-340 redox system and compares with blank (absence of bacteria) experiment.
Figure 19:
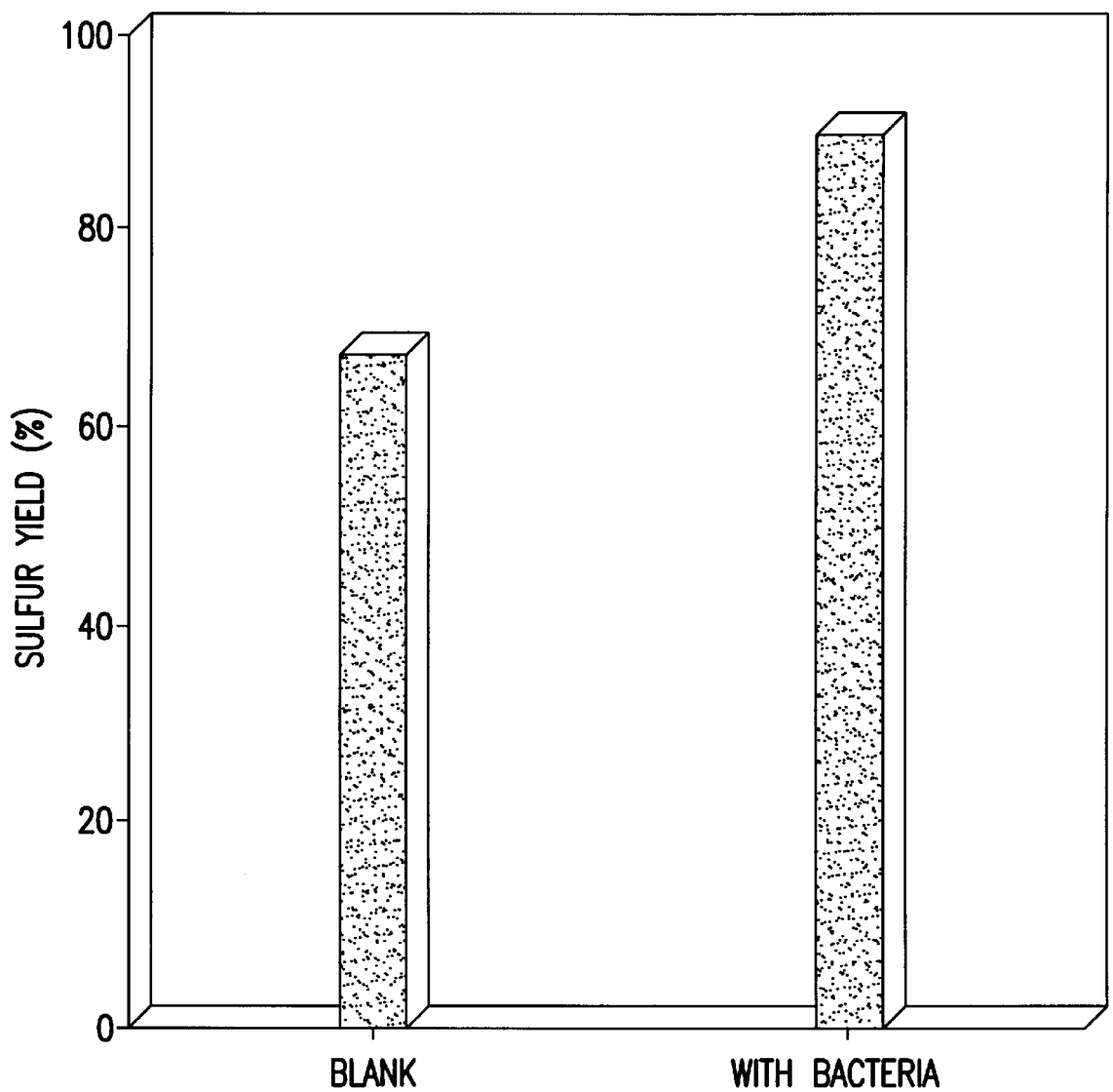
FIG. 19 is a graph illustrating the effect of *Tf.* culture incubated in ARI-340 solution at 35° C. for zero days and evaluated for its sulfur recovery capability (percent of theoretical) at 25° C. and pH 8.5, in ARI-340 redox system and compares with blank (absence of bacteria) experiment.
Figure 20:
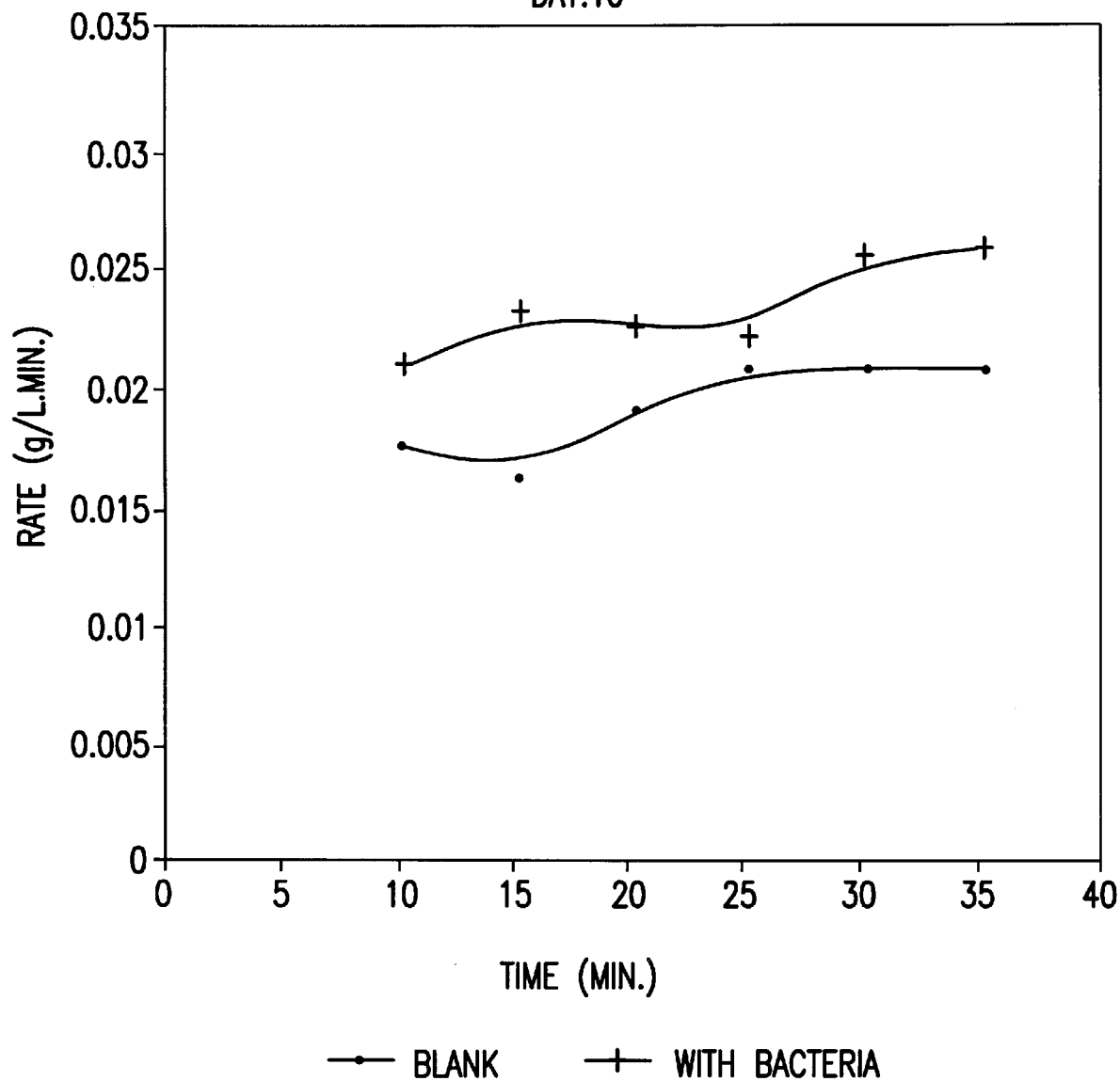
FIG. 20 is a graph illustrating the effect of *Thiobacillus ferrooxidans* culture incubated in ARI-340 solution at 35° C. for 10 days and evaluated for its ferric ion regeneration rate (mg/L. min) at 25° C. and pH 8.5, as a function of time and compares with blank (absence of bacteria) experiment.
Figure 21:
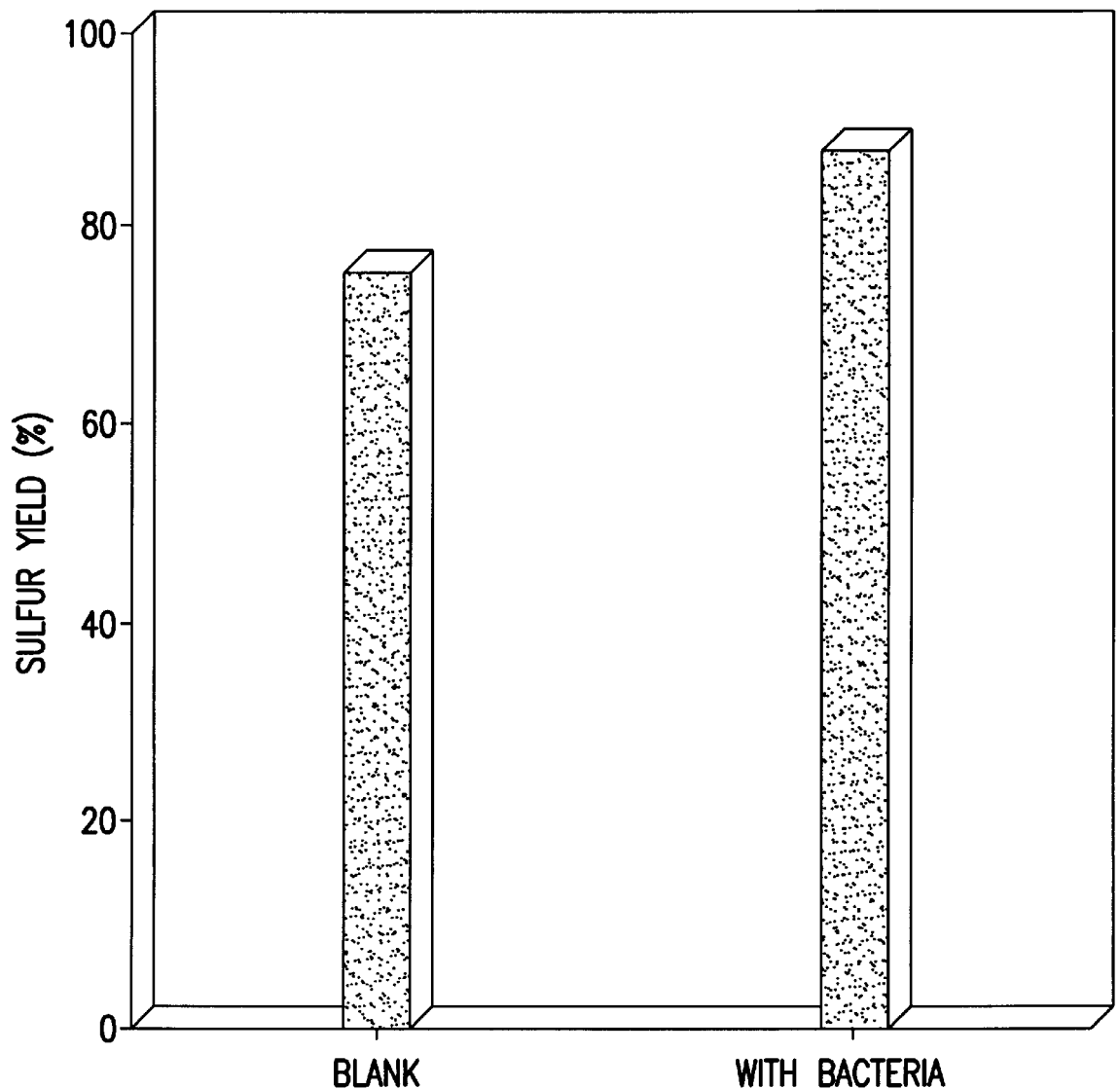
FIG. 21 is a graph illustrating the effect of *Tf.* culture incubated in ARI-340 at 35° C. for 10 days and evaluated for its sulfur recovery capability (percent of theoretical) at 25° C. and pH 8.5, in ARI-340 redox system and compares with blank (absence of bacteria) experiment.

The samples were subjected to one cycle runs before incubation and at the end of the 10-day incubation period. They were used for oxidation of hydrogen sulfide and subsequent reoxidation to the ferric state. FIGS. 18 and 19 compare the regeneration rates and sulfur recovery at zero day for the blank sample and the sample containing *T. ferrooxidans*. FIGS. 20 and 21 compare the rates and sulfur recovered at the tenth day.

6. Thermal Degradation Studies With LO-CAT 310 and LO-CAT 340 in Presence of *Thiobacillus ferrooxidans* at 35° C.

Six samples of LO-CAT 310 without *T. ferrooxidans* (blank) and incubated with *T. ferrooxidans* at 35° C. and samples at 0, 5 and 10-day intervals were blanketed with nitrogen and studied. Another set of six samples of LO-CAT 340 without *T. ferrooxidans* (blank) and with *T. ferrooxidans* incubated at 35° C. and sampled at 0, 5 and 10-day intervals were blanketed with nitrogen and studied.

7. Thermal Stability of *T. ferrooxidans* in Redox Solutions Using LO-CAT 310 at 40° C.

Two sets of samples containing 907 ppm of total iron in LO-CAT 310 were incubated at 40° C. and an initial pH of 7.75 for ten days. The $Fe^{2+}$, $Fe^{3+}$ concentrations, pH and redox potential were monitored daily for the control (blank) sample without bacteria and $Fe^{2+}$, Fe3+, pH, redox potential and *T. ferrooxidans* cell density were monitored for the sample inoculated with *T. ferrooxidans* cells containing $1 \times 10^{11}$ cells/Liter.

Figure 22:
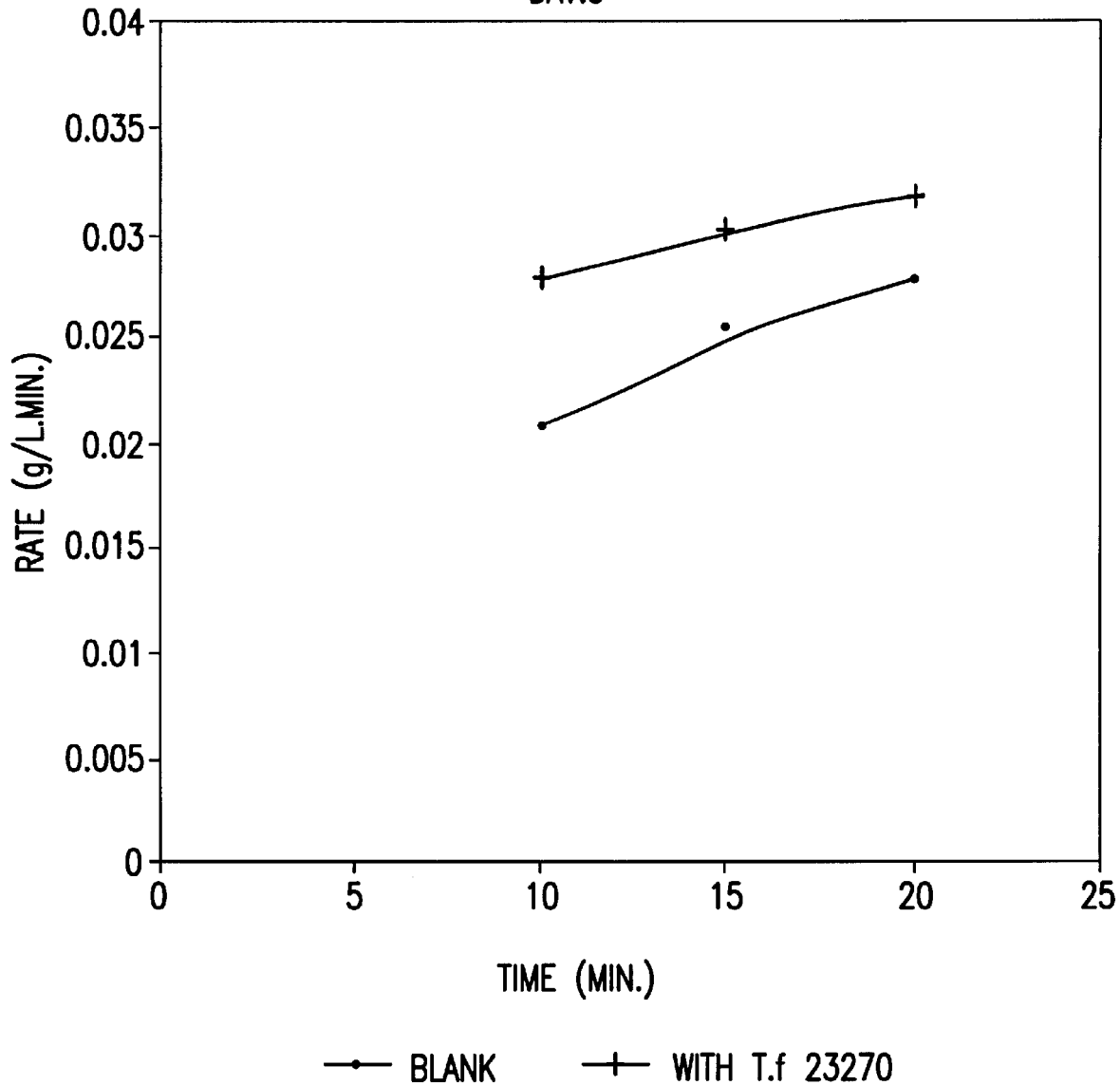
FIG. 22 is a graph illustrating the effect of *Thiobacillus ferrooxidans* culture incubated in ARI-310 solution at 40° C. for 5 days and evaluated for its ferric ion regeneration rate (mg/L. min) at 25° C. and pH 8.5, in ARI-310 redox system and compares with blank (absence of bacteria) experiment.
Figure 23:
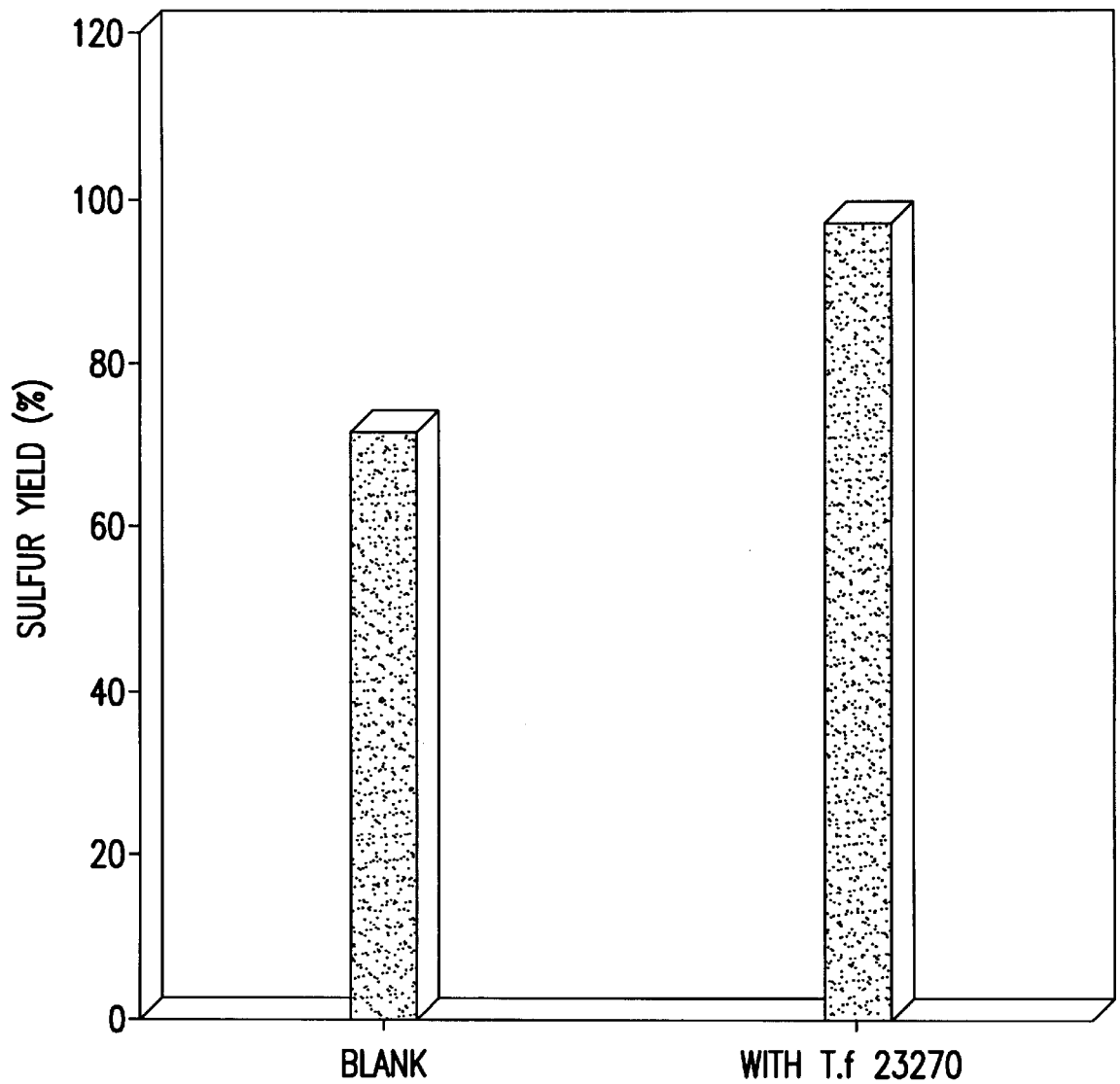
FIG. 23 is a graph illustrating the effect of *Thiobacillus ferrooxidans* culture incubated in ARI-310 solution at 40° C. for 5 days and evaluated for its sulfur recovery capability (percent of theoretical) at 25° C. and pH 8.5, in ARI-310 redox system and compares with blank (absence of bacteria) experiment.
Figure 24:
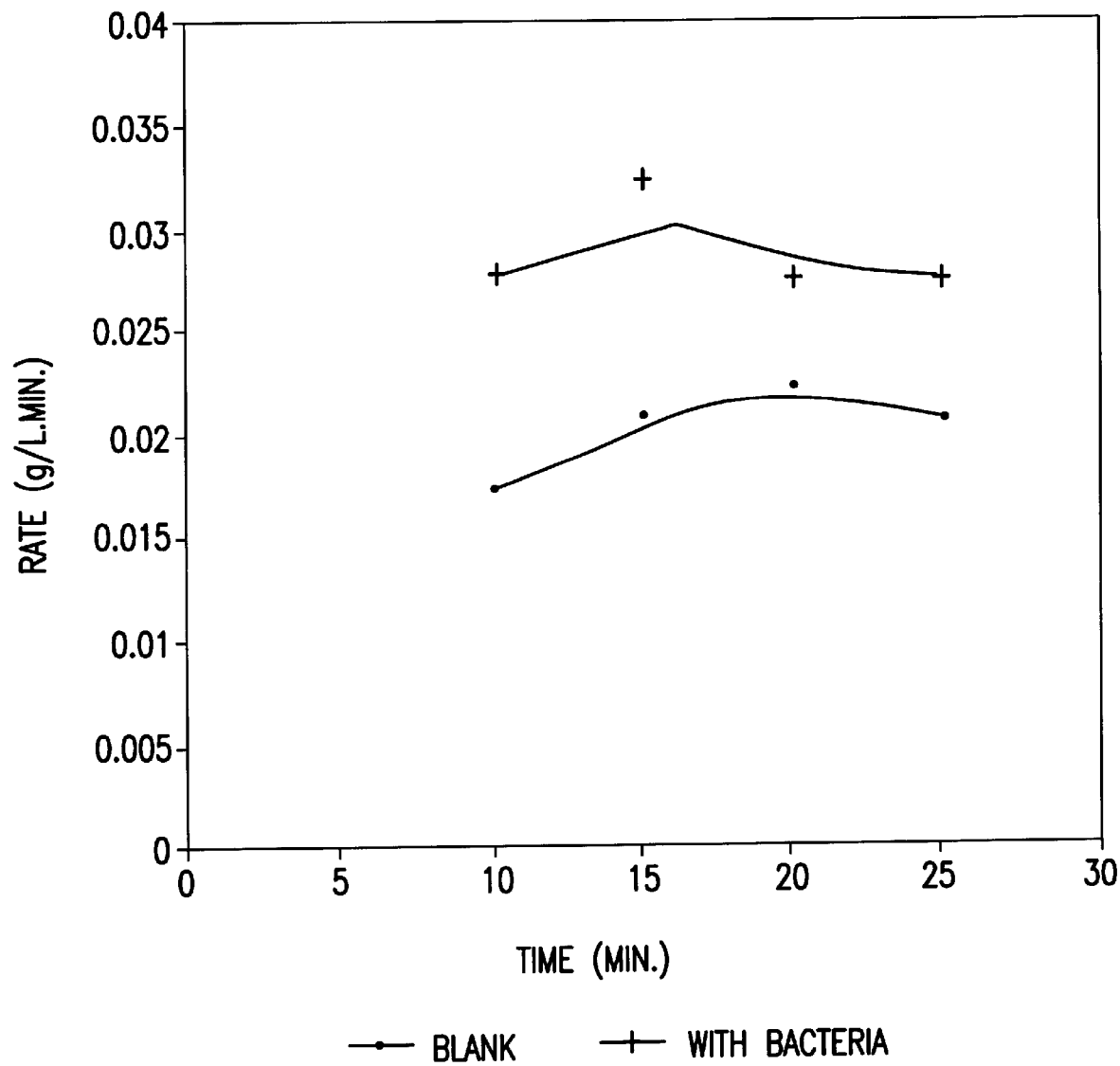
FIG. 24 is a graph illustrating the effect of *Thiobacillus ferrooxidans* culture incubated in ARI-310 solution at 40° C. for 10 days and evaluated for its ferric ion regeneration rate (mg/L. min) at 25° C. and pH 8.5, as a function of time in the ARI-310 redox system and compares with blank (absence of bacteria) experiment.
Figure 25:
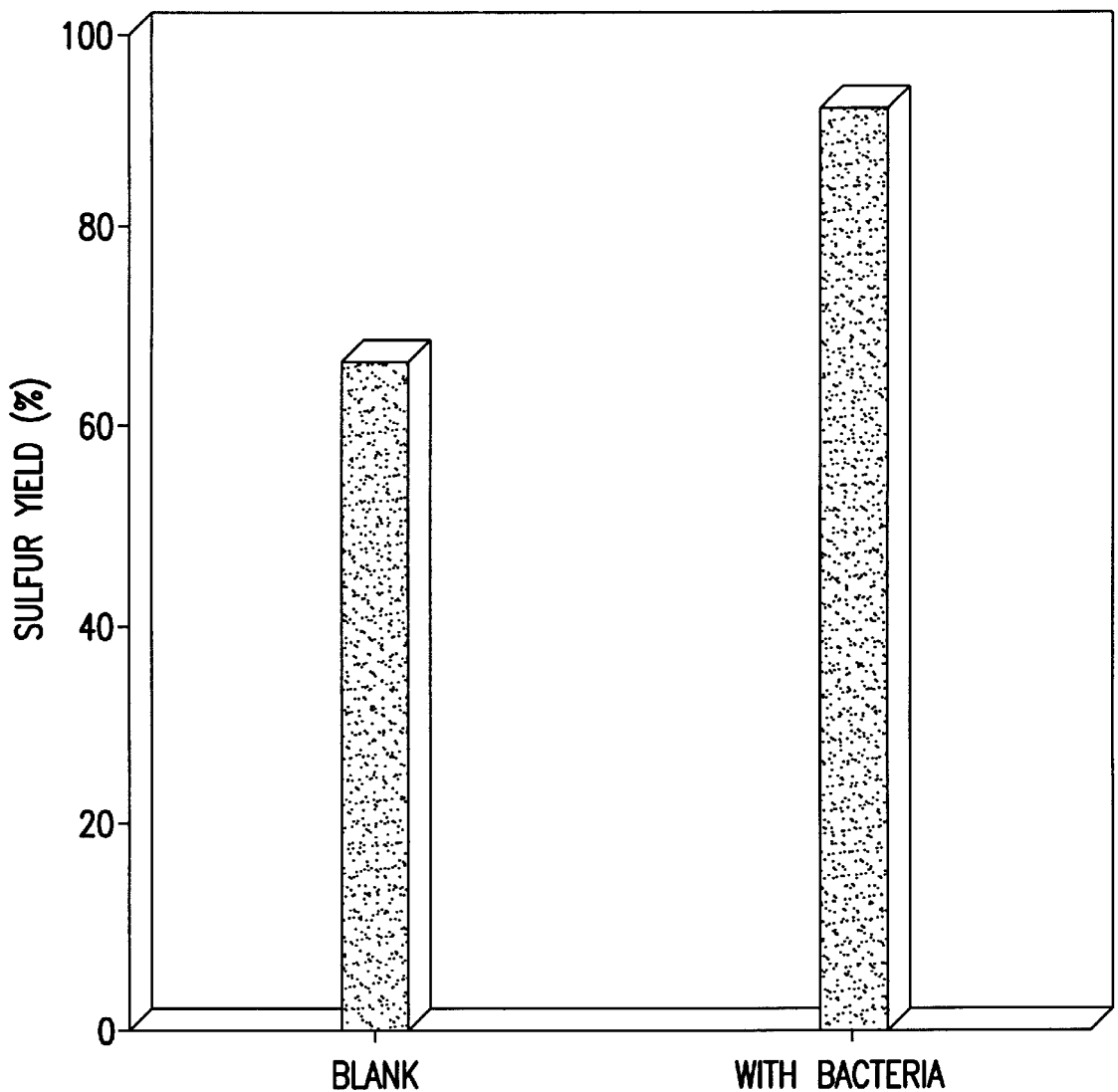
FIG. 25 is a graph illustrating the effect of *Thiobacillus ferrooxidans* culture incubated in ARI-310 solution at 40° C. for 10 days and evaluated for its sulfur recovery capability (percent of theoretical) at 25° C. and pH 8.5, and compares with blank (absence of bacteria) experiment.

After 5-, and 10-day incubation periods, the LO-CAT 310 blanks and the LO-CAT 310 containing *T. ferrooxidans* were used for oxidation of hydrogen sulfide and subsequent reoxidation of the reduced LO-CAT 310 to the ferric state. FIGS. 22 and 23 compare the rates and sulfur recovered at the fifth day for the blank sample and the sample containing *T. ferrooxidans*. FIGS. 24 and 25 compare the rates and sulfur recovered at the tenth day.

8. Thermal Stability of *T. ferrooxidans* in Redox Solutions Using LO-CAT 340 at 40° C.

Two sets of samples containing 1033 ppm of total iron in LO-CAT 340 were incubated at 40° C. and an initial pH of 7.75 and kept in an incubator for ten days. The $Fe^{2+}$, $Fe^{3+}$ concentrations, pH, and redox potential were monitored daily for the control sample without bacteria (blank) and $Fe^{2+}$, $Fe^{3+}$, pH, redox potential and *T. ferrooxidans* cell density were monitored for the samples inoculated with *T. ferrooxidans* cells containing $1.0 \times 10^{11}$ cells/Liter initially.

Figure 26:
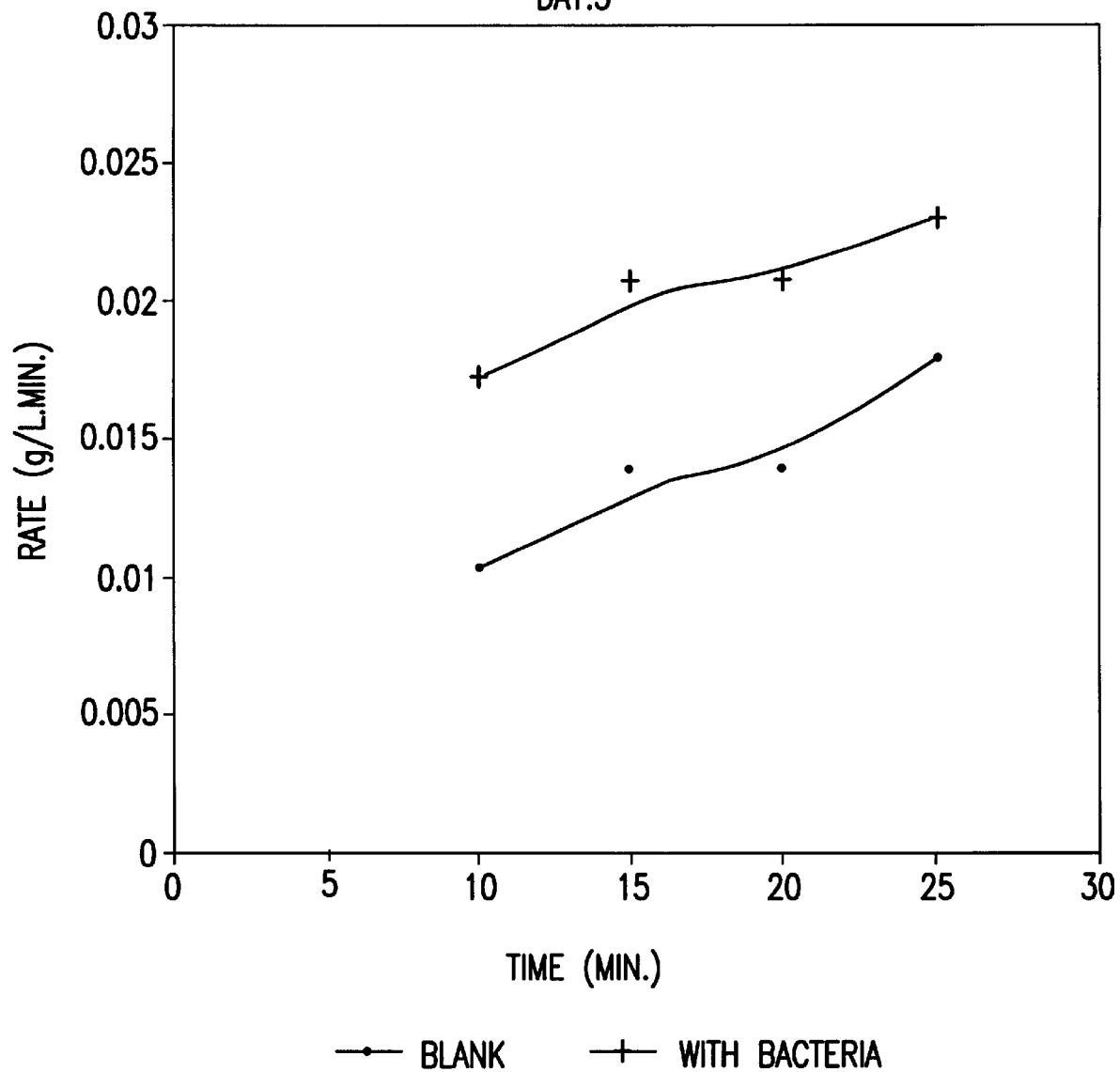
FIG. 26 is a graph illustrating the effect of *Thiobacillus ferrooxidans* culture incubated in ARI-340 solution at 40° C. for 5 days and evaluated for its ferric ion regeneration rate (mg/L. min) at 25° C. and pH 8.5, as a function of time in ARI-340 redox system and compares with blank (absence of bacteria) experiment.
Figure 27:
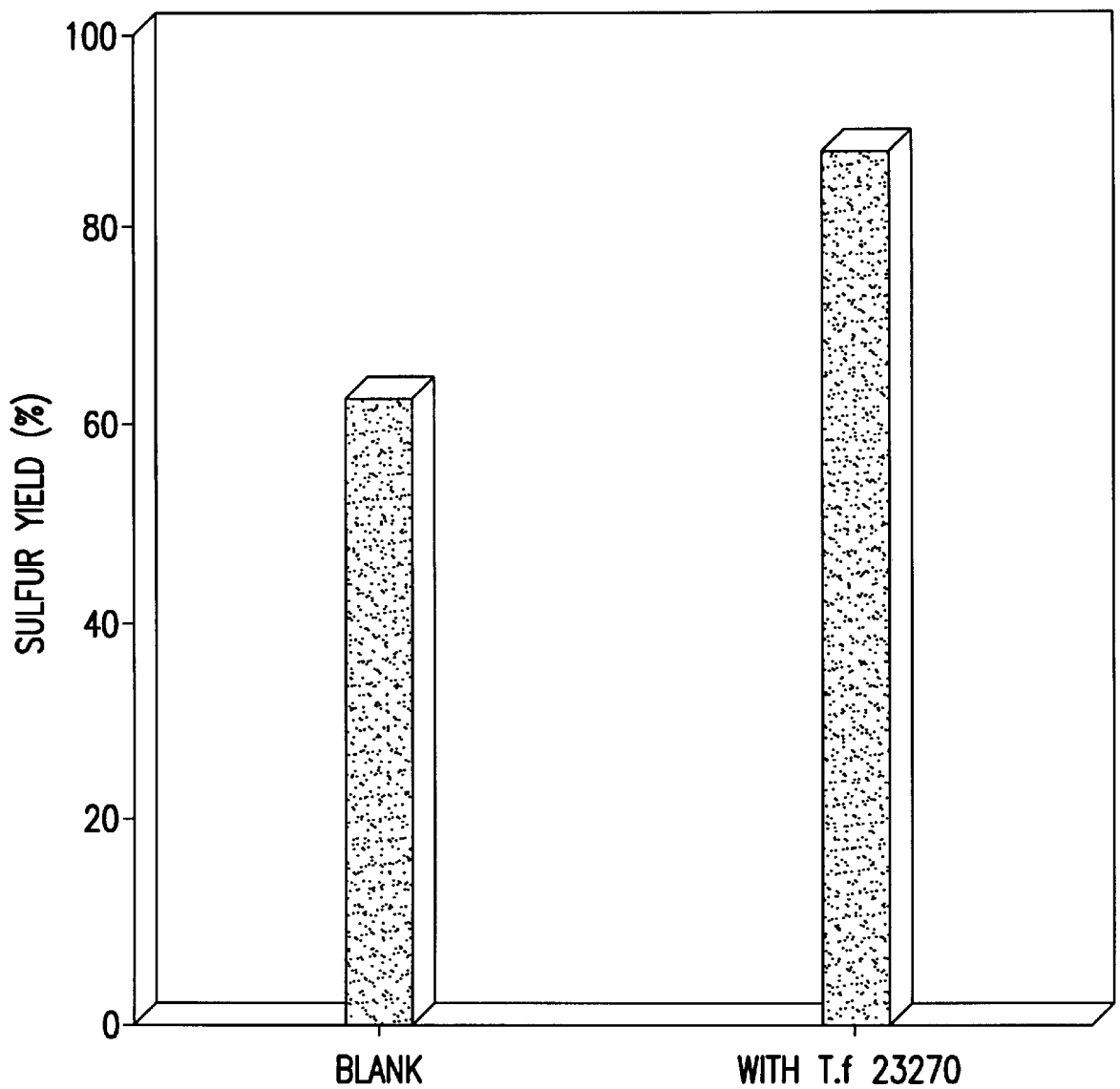
FIG. 27 is a graph illustrating the effect of *Thiobacillus ferrooxidans* culture incubated in ARI-340 solution at 40° C. for 5 days and evaluated for its sulfur recovery capability (percent of theoretical) at 25° C. and pH 8.5, in ARI-340 redox system and compares with blank (absence of bacteria) experiment.
Figure 28:
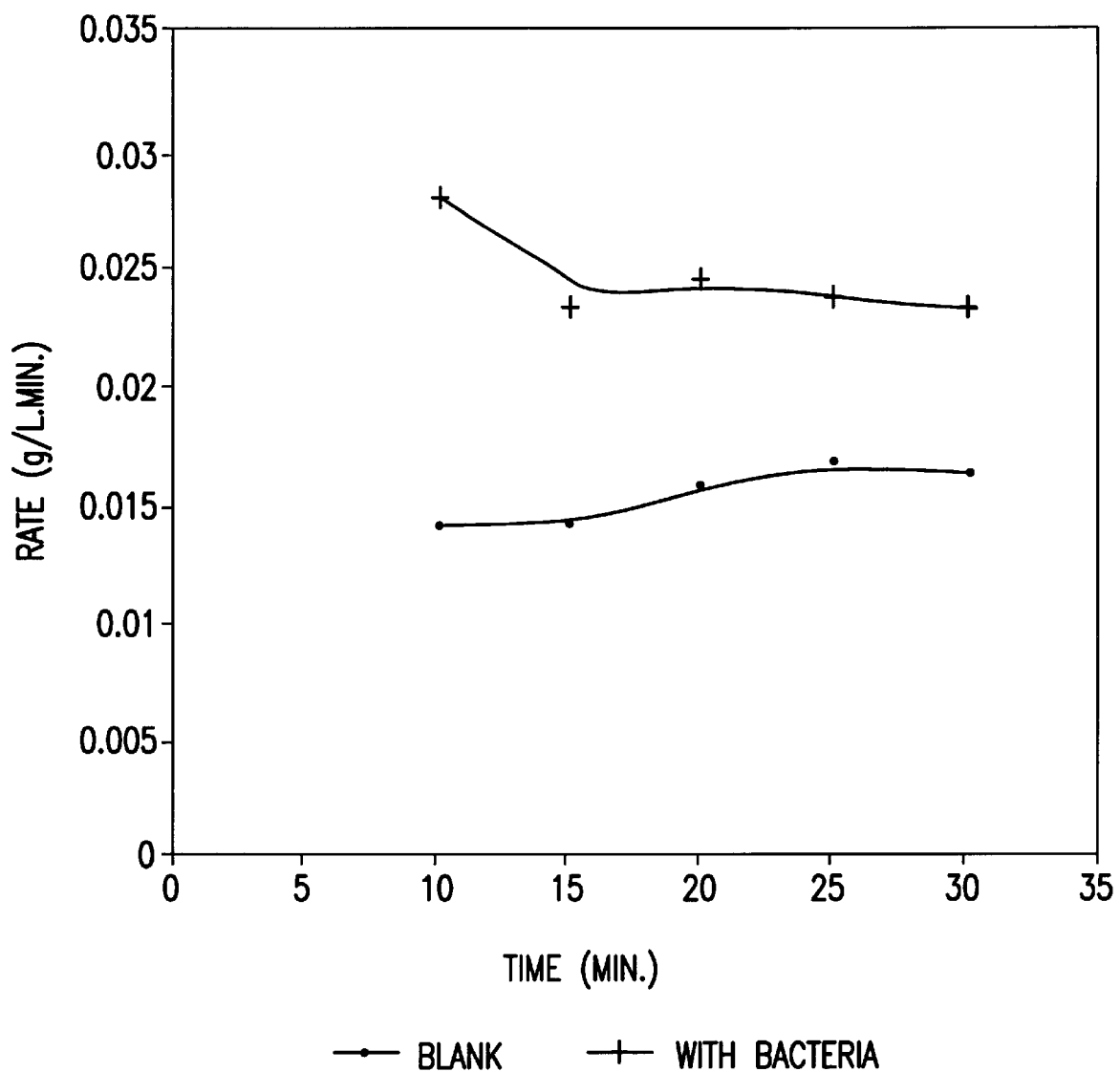
FIG. 28 is a graph illustrating the effect of *Thiobacillus ferrooxidans* culture incubated at 40° C. for 10 days in ARI-340 solution and evaluated for its ferric ion regeneration rate (mg/L. min) at 25° C. and pH 8.5, as a function of time in ARI-340 redox system and compares with blank (absence of bacteria) experiment.
Figure 29:
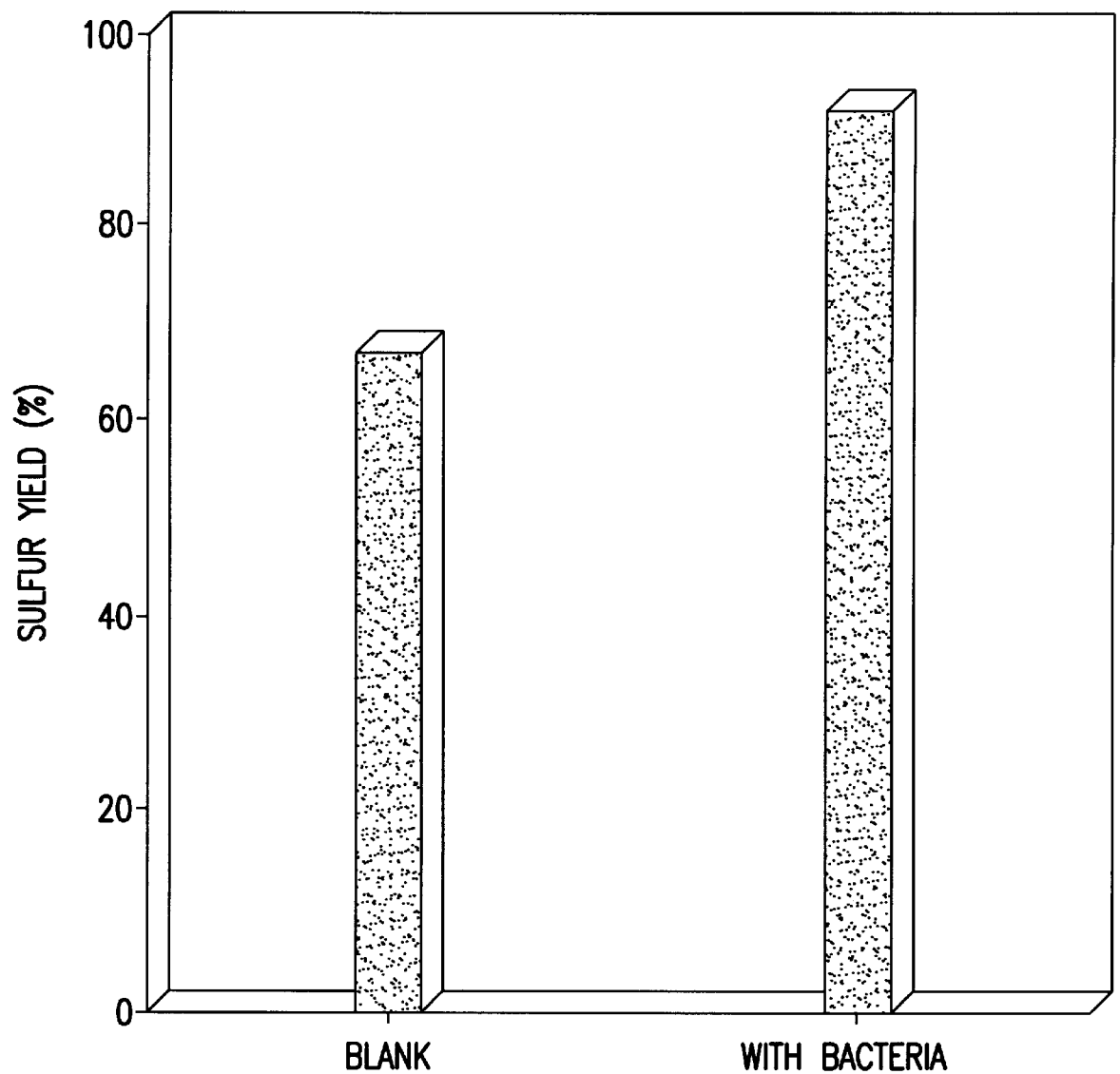
FIG. 29 is a graph illustrating the effect of *Thiobacillus ferrooxidans* culture incubated in ARI-340 solution at 40° C. for 10 days and evaluated for its sulfur recovery capability (percent of theoretical) at 25° C. and pH 8.5, in ARI-340 redox system and compares with blank (absence of bacteria) experiment.

The samples incubated for 5- and 10-days containing LO-CAT 340 without bacterial (blank) and with *T. ferrooxidans* were used for oxidation of hydrogen sulfide and subsequent reoxidation of the reduced LO-CAT 340 to the ferric state. FIGS. 26 and 27 compare the regeneration rates and sulfur recovered at the fifth day for the blank sample and the sample containing *T. ferrooxidans*. FIGS. 28 and 29 compare the rates and sulfur recovered at the tenth day.

9. Thermal Degradation Studies with LO-CAT 310 in Presence of *Thiobacillus ferrooxidans* at 40° C.

Six samples of LO-CAT 310 without *T. ferrooxidans* (blank) and with *T. ferrooxidans* incubated at 40° C. and sampled at 0, 5 and 10-day intervals were blanketed with nitrogen and studied. Another set of six samples of LO-CAT 340 without *T. ferrooxidans* (blank) and with *T. ferrooxidans* incubated at 40° C. and sampled at 0, 5 and 10-day intervals were blanketed with nitrogen and studied.

The thermal stability of high pH *Thiobacillus ferrooxidans* in liquid redox solutions was compared to that of solutions without *Thiobacillus ferrooxidans* as reflected in FIGS. 10–29.

The foregoing results indicate that high pH *Thiobacillus ferrooxidans* provides enhanced thermal stability to the liquid redox catalysts against degradation at temperatures of 25°–50° C.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claims, including the full range of equivalency to which each element is entitled.

I claim:

1. A process for biologically assisting an iron-based redox process for catalytic oxidation of a sulfide compound from a gas in a redox system wherein said catalyst comprises a ferric compound and at least one organic chelant capable of holding ferric and ferrous ions in solution at processing temperatures and conditions suitable for generation and retrieval of elemental sulfur, said process comprising the steps of:

a) oxidation of a sulfide compound with a redox system comprising ferric ions;

b) removal of elemental sulfur from said system; and c) reoxidation of ferrous ions in the redox system in the presence of a culture of bacteria comprising *Thiobacillus ferrooxidans* and *Leptospirillum ferrooxidans,* said reoxidation being conducted at a pH at least as high as about pH 7.5.

2. A process according to claim 1 wherein said redox system is operable at processing temperatures in the range from about 25 to about 50 degrees C.

3. A process according to claim 1 wherein said elemental sulfur is removed from said redox system by filtration.

4. A process for biologically assisting an iron-based redox process for catalytic oxidation of hydrogen sulfide from a gas in a redox system wherein said catalyst comprises a ferric compound and at least one organic chelant capable of holding ferric and ferrous ions in solution at processing temperatures and conditions suitable for generation and retrieval of elemental sulfur, characterized by reduced degradation of said catalyst, said process comprising the steps of:

a) oxidation of hydrogen sulfide by bubbling a hydrogen sulfide containing gas through a redox system comprising ferric ions;

b) removal of elemental sulfur from said system; and c) reoxidation of ferrous ions in the redox system in the presence of a mixed culture of bacteria, said mixed culture not effecting substantial degradation of a polyhydroxylated saccharide component of said catalyst, said reoxidation being conducted at a pH at least as high as about pH 7.5.

5. A process according to claim 4, wherein said polyhydroxylated saccharide component of said catalyst comprises sorbitol.

6. A process for biologically assisting an iron-based redox process for catalytic oxidation of hydrogen sulfide from a gas in a redox system wherein said catalyst comprises a ferric compound and at least one organic chelant capable of holding ferric and ferrous ions in solution at processing temperatures and conditions suitable for generation and retrieval of elemental sulfur, characterized by reduced degradation of said catalyst, said process comprising the steps of:

a) oxidation of a hydrogen sulfide by bubbling a hydrogen sulfide containing gas through a redox system comprising ferric ions;

b) removal of elemental sulfur from said system; and c) reoxidation of ferrous ions in the redox system in the presence of a mixed culture of bacteria comprising *Thiobacillus ferrooxidans* and at least one other acidophilic bacteria, said mixed culture not effecting substantial degradation of nitrilotriacetic acid in said catalyst, said reoxidation being conducted at a pH at least as high as about pH 7.5.

7. A process for biologically assisting an iron-based redox process for catalytic oxidation of hydrogen sulfide from a gas in a redox system wherein said catalyst comprises a ferric compound and at least one organic chelant capable of holding ferric and ferrous ions in solution, said process comprising the steps of:

a) oxidation of hydrogen sulfide by bubbling a hydrogen sulfide containing gas through a redox system comprising ferric ions;

b) removal of elemental sulfur from said system; and c) reoxidation of ferrous ions in the redox system in the presence of a culture of acidophilic bacteria wherein said presence of said bacteria permit processing temperatures within the redox system to be increased from about 25 to about 50 degrees C. said reoxidation being conducted at a pH at least as high as about pH 7.5.

8. A process according to claim 7, wherein the functional stability of said catalyst is maintained at said increased processing temperatures.

9. A process for biologically assisting an iron-based redox process for catalytic oxidation of a sulfide compound from a gas in a redox system wherein said catalyst comprises a ferric compound and at least one organic chelant capable of holding ferric and ferrous ions in solution at processing temperatures and conditions suitable for generation and retrieval of elemental sulfur, said process comprising the steps of:

a) oxidation of a sulfide compound with a redox system comprising ferric ions;

b) removal of elemental sulfur from said system; and c) reoxidation of ferrous ions in the redox system in the presence of a culture of bacteria comprising *Leptospirillum ferrooxidans,* said reoxidation being conducted at a pH at least as high as about pH 7.5.

* * * * *